US 6,544,258 B2

(12) United States Patent
Fleenor et al.

(10) Patent No.: US 6,544,258 B2
(45) Date of Patent: Apr. 8, 2003

(54) PRESSURE SORE PAD HAVING SELF-LIMITING ELECTROSURGICAL RETURN ELECTRODE PROPERTIES AND OPTIONAL HEATING/COOLING CAPABILITIES

(75) Inventors: Richard P. Fleenor, Englewood, CO (US); David B. Kieda, Salt Lake City, UT (US); James D. Isaacson, Salt Lake City, UT (US); Paul R. Borgmeier, Salt Lake City, UT (US)

(73) Assignee: Mega-Dyne Medical Products, Inc., Draper, UT (US)

( * ) Notice: Subject to any disclaimer, the term of this patent is extended or adjusted under 35 U.S.C. 154(b) by 69 days.

(21) Appl. No.: 09/773,282

(22) Filed: Jan. 31, 2001

(65) Prior Publication Data

US 2001/0029367 A1 Oct. 11, 2001

Related U.S. Application Data

(63) Continuation-in-part of application No. 09/569,998, filed on May 12, 2000, now Pat. No. 6,454,764, which is a continuation-in-part of application No. 09/201,998, filed on Nov. 30, 1998, now Pat. No. 6,083,221, which is a continuation-in-part of application No. 08/741,468, filed on Oct. 30, 1996, now abandoned.

(51) Int. Cl.$^7$ .............................................. A61B 18/16
(52) U.S. Cl. ........................ 606/32; 606/35; 607/152; 128/908
(58) Field of Search ...................... 606/32, 35, 39; 607/152; 128/908

(56) References Cited

U.S. PATENT DOCUMENTS

| | | | |
|---|---|---|---|
| 3,089,496 A | 5/1963 | Degelman | 128/303 |
| 3,543,760 A | 12/1970 | Bolduc | 128/416 |
| 3,720,209 A | 3/1973 | Bolduc | 128/2 |
| 3,848,600 A | 11/1974 | Patrick, Jr. et al. | 128/303 |
| 4,088,133 A | 5/1978 | Twentier | 128/303 |
| 4,092,985 A | 6/1978 | Kaufman | 128/303 |
| 4,094,320 A | 6/1978 | Newton et al. | 128/303 |
| 4,117,846 A | 10/1978 | Williams | 128/303 |
| 4,166,465 A | 9/1979 | Esty et al. | 128/303 |
| 4,200,104 A | 4/1980 | Harris | 128/303 |
| 4,207,904 A | 6/1980 | Greene | 128/798 |

(List continued on next page.)

FOREIGN PATENT DOCUMENTS

GB        1480736        7/1977

OTHER PUBLICATIONS

Wald et al., "Accidental Burns Associated With Electrocautery," JAMA, Aug. 16, 1971, vol. 217, No. 7, pp. 916–921.

Primary Examiner—Lee Cohen
(74) Attorney, Agent, or Firm—Workman, Nydegger & Seeley

(57) ABSTRACT

A self-limiting electrosurgical electrode for use with electrosurgery and various other surgical procedures. The electrode can include a pad and a conductive element that collectively has an effective bulk impedance equal to or greater than about 4,000 Ω·cm. The effective bulk impedance of the electrode arises from resistive components, capacitive components, inductive components, or combinations thereof of both the pad and the conductive element. Through the selection of the impedance characteristics for the electrode materials, and through tailoring of electrode geometries, the electrode of the present invention is self-regulating and self-limiting as to current density and temperature rise so as to prevent patient trauma. Additionally, the selection of materials and electrode geometries can prevent the creation of pressure sore or decubitus ulcers on a patient resting upon the electrode. Further, alternate configurations of the electrosurgical electrode can heat and/or cool a patient during the performance of a surgical procedure.

45 Claims, 12 Drawing Sheets

U.S. PATENT DOCUMENTS

| | | | |
|---|---|---|---|
| 4,226,247 A | 10/1980 | Hauser et al. | 128/641 |
| 4,231,372 A | 11/1980 | Newton | 128/303 |
| 4,237,886 A | 12/1980 | Sakurada et al. | 128/303 |
| 4,237,887 A | 12/1980 | Gonser | 128/303 |
| 4,267,840 A | 5/1981 | Lazar et al. | 128/303 |
| 4,304,235 A | 12/1981 | Kaufman | 128/303 |
| 4,384,582 A | 5/1983 | Watt | 128/303 |
| 4,387,714 A | 6/1983 | Geddes et al. | 128/303 |
| 4,669,468 A | 6/1987 | Cartmell et al. | 128/303 |
| 4,770,173 A | 9/1988 | Feucht et al. | 128/303 |
| 4,799,480 A | 1/1989 | Abraham et al. | 128/303 |
| 5,352,315 A | 10/1994 | Carrier et al. | 156/267 |
| 5,354,790 A * | 10/1994 | Keusch et al. | 607/152 |
| 5,520,683 A | 5/1996 | Subramaniam et al. | 606/32 |
| 5,836,942 A | 11/1998 | Netherly et al. | 606/32 |
| 6,053,910 A | 4/2000 | Fleenor | 606/32 |
| 6,083,221 A * | 7/2000 | Fleenor et al. | 606/32 |

* cited by examiner

PRESSURE SORE PAD HAVING SELF-LIMITING ELECTROSURGICAL RETURN ELECTRODE PROPERTIES AND OPTIONAL HEATING/COOLING CAPABILITIES

THE PRIOR STATE OF THE ART

This is a continuation-in-part application of U.S. patent application Ser. No. 09/569,998, filed May 12, 2000 now U.S. Pat. No. 6,454,764, and entitled "Self-Limiting Electrosurgical Return Electrode," that is a continuation-in-part application of U.S. patent application Ser. No. 09/201,998, filed Nov. 30, 1998 now U.S. Pat. No. 6,083,221, and entitled "Resistive Reusable Electrosurgical Return Electrode," that is a continuation-in-part application of U.S. patent application Ser. No. 08/741,468, filed Oct. 30, 1996 now abandoned, and entitled "Reusable Electrosurgical Return Pad." Reference is made to co-pending U.S. patent application Ser. No. 09/435,498, filed Oct. 6, 1999, and entitled "Capacitive Reusable Electrosurgical Return Electrode", and U.S. patent application Ser. No. 08/741,469, filed Oct. 30, 1996, and entitled "Capacitive Reusable Electrosurgical Return Electrode," the disclosures of which are incorporated by this reference.

BACKGROUND OF THE INVENTION

1. The Field of the Invention

This invention relates to both electrosurgery and pressure sore pads. More particularly, this invention relates to pressure sore pads that conform to a patient's body to minimize the incidence of decubitus ulcers or pressure sores, while being capable of acting as an effective and safe electrosurgical energy return without the need for conducting or dielectric gels.

2. The Relevant Technology

It is well known in the medical field that patients may develop decubitus ulcers, also known as pressure sores during a prolonged period of immobility. Typically, pressure sores develop in elderly patients who are confined to their beds or otherwise have limited movement. The pressure sores arise in those areas of the patient's body where a prolonged pressure is applied to the patient's tissue, usually over an underlying bony prominence. The prolonged pressure causes ischemic damage and tissue necrosis due to the maintenance of blood pressure above the normal capillary blood pressure of 32 mmHg. Although pressure sores typically occur in those patients who remain in one position for an extended period of time, pressure sores may arise from application of an intense pressure applied over a short period of time, approximately two hours, to a localized area, such as during various surgical procedures.

Generally, to prevent pressure sores the position of the patient is frequently changed to provide relief to the patient's tissue. Additionally, the patient may rest upon one of a variety of mattresses or pads, such as foam pads, sheepskin layers, air filled mattresses, water mattresses, and the like, that reduce the pressure applied to the sensitive areas of the patient's body, such as tissue over an underlying bony prominence. Although it is desirable to reposition the patient every 2 hours, whether or not the patient is lying on a pressure reducing mattress or pad, this is often difficult to perform during various surgical procedures, such as during electrosurgical procedures.

During an electrosurgical procedure, radio frequency (RF) power is employed to cut tissue and coagulate bleeding encountered in performing surgical procedures. For historical perspective and details of such techniques, reference is made to U.S. Pat. No. 4,936,842, issued to D'Amelio et al., and entitled "Electrosurgical Probe Apparatus," the disclosure of which is incorporated by this reference.

As is known to those skilled in the medical arts, electrosurgery is widely used and offers many advantages including the use of a single surgical tool for both cutting and coagulation. Every monopolar electrosurgical generator system, however, must have an active electrode that is applied by the surgeon to the patient at the surgical site to perform surgery and a return path from the patient back to the generator. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. If a relatively high current density is produced at the return electrode, the temperature of the patient's skin and tissue will rise in this area and can result in an undesirable patient burn. According to the Emergency Care Research Institute, a well-known medical testing agency, the heating of body tissue to the threshold of necrosis occurs when the current density exceeds 100 milliamperes per square centimeter. Furthermore, the Association for the Advancement of Medical Instrumentation ("AAMI") has published standards that require that the maximum patient surface tissue temperature adjacent an electrosurgical return electrode shall not rise more than six degrees (6°) Celsius under stated test conditions.

Over the past twenty years, industry has developed products in response to the medical need for a safer return electrode in two major ways. First, they went from a small, about 12×7 inches, flat stainless steel plate coated with a conductive gel placed under the patient's buttocks, thigh, shoulders, or any location where gravity can ensure adequate contact area to a flexible electrode. These flexible electrodes, which are generally about the same size as the stainless steel plates, are coated with a conductive or dielectric polymer and have an adhesive border on them so they will remain attached to the patient without the aid of gravity. Upon completion of the electrosurgical procedure, these flat flexible electrodes are disposed of. By the early 1980's, most hospitals in the United States had switched over to using this type of return electrode. These return electrodes are an improvement over the old steel plates and resulted in fewer patient return electrode burns but have resulted in additional surgical costs in the United States of several tens of millions of dollars each year. Even with this improvement, hospitals were still experiencing some patient burns caused by electrodes that would accidentally fall off or partially separate from the patient during surgery.

Subsequently, there was proposed a further improvement, an Electrode Contact Quality Monitoring System that would monitor the contact area of the electrode that is in contact with the patient and turn off the electrosurgical generator whenever there was insufficient contact area. Such circuits are shown, for example, in U.S. Pat. No. 4,231,372, issued to Newton, and entitled "Safety Monitoring Circuit for Electrosurgical Unit," the disclosure of which is incorporated by this reference. This system has resulted in additional reduction in patient return electrode burns, but requires a special disposable electrode and an added circuit in the generator that drives the cost per procedure even higher. Fifteen years after this system was first introduced, fewer than 40 percent of all the surgical operations performed in the United States use this system because of its high costs.

Although various advances have been made in the electrosurgical arts, as discussed previously, there remains problems associated with preventing the creation of pressure sores during electrosurgical and other surgical procedures.

As briefly mentioned above, typically, a patient is placed upon a pressure reducing mattress or pad during a surgical procedure to reduce or substantially eliminate the forces applied to the sensitive areas of the body where tissue covers underlying bony prominences. One device that may be used to prevent pressure sores in an operational scenario is a foam pad, approximately 3–4 inches in height, which is placed between the operating table and the patient. Although foam pads have many advantages, such as being inexpensive and lightweight, they provide minimal relief to the patient while trapping body heat that may aid in generating pressure sores. Furthermore, by trapping heat the foam pad may aid in increasing the patient's tissue temperature so that during an electrosurgical procedure the tissue temperatures may rise above the six degrees (6°) Celsius temperature rise required by the AAMI. Additionally, foam pads are typically discarded proceeding a surgical procedure since they are difficult to sterilize and clean. Furthermore, the material forming the foam pad may release lethal fumes if ignited during a fire.

An alternate pressure reducing mattress or pad is a layer of sheepskin placed on the operating table. Unfortunately, sheepskin provides poor protection to the patient and does not effectively distribute the patient's pressure throughout the entire surface upon which they are laying. As with the foam pad discussed above, sheepskin is difficult to sterilize and clean following a surgical procedure.

Yet another type of pressure reducing device is the air inflated mattress that includes a vinyl sleeve filled with air to a desired pressure. Unfortunately, the air mattress must be significantly pressurized to prevent the patient from touching the bottom surface upon which the mattress is placed. In the event the patient touches the bottom surface, there is a chance for development of a pressure sore. Additionally, in order to maintain the required pressure, typically, a pump is connected to the mattress to monitor the pressure of air contained within the mattress and pump additional air into the mattress as required. With a patient placed upon the movable air mattress, which is in turn resting upon an operating table, the patient is lying upon two flexible surfaces. The patent is thereby placed in an unstable and precarious position during surgical procedures. Additionally, air-type mattresses are expensive to maintain due to the need for a pump to maintain the required air pressure. Furthermore, the air mattress may easily be perforated, thereby leaking air and reducing the effectiveness of the mattress to maintain the patient distal from the surface upon which the mattress is placed.

A similar pressure-reducing device to the air filled mattress is the water type mattress. The water-type mattress has a similar form to that of the air mattress; however, water is pumped through the mattress rather than air. Unfortunately, the water type mattress suffers from many of the limitations of the air type mattress. Additionally, in the event that the water mattress leaks, a large amount of water would be discharged onto the floor surrounding the patient, thereby making it dangerous for individuals to walk and work in close proximity to the patient.

Although many of the above-described limitations are alleviated in general use within a hospital, each recited pressure sore device has various drawbacks with respect to their use during electrosurgical procedures. For example, in the event a foam type mattress is used during an electrosurgical procedure, there is a chance that the foam pad may ignite, thereby burning the patient and also emitting lethal fumes within the operating theater.

With respect to the air and water type mattresses, inclusion of the required pumps to maintain the desired pressure for a long period of time increases the amount of equipment necessary stored within an operating theater. As such, with more equipment within a limited space the ability of the surgeon to move around reduces. In the event of a water leak from the water mattress, there is the possibility that of electrocution of the patient and/or the physicians and nurses in the operating theater as well as the possibility of shorting of the electrosurgical return electrode.

Therefore, it would be an advance in the present electrosurgical art to provide an electrosurgical electrode that is self-limiting, while reducing the pressure sore creation.

SUMMARY OF THE INVENTION

The present invention overcomes the problems of the prior art by providing a return electrode that eliminates patient burns without the need for expensive disposable electrodes and monitoring circuits in specialized RF generators, while also providing a pressure sore pad that minimizes the occurrence of pressure sores for patients having electrosurgical procedures.

Briefly, the improved return electrode according to the preferred embodiment of the invention hereof includes an effective surface area that is larger than other return electrodes that have been disclosed or used in surgery previously. It is so large and so adapted for positioning relative to the body of a patient that it eliminates the need for conductive or dielectric gels. Moreover, the exposed surface is of a material that is readily washable, disenfectable, and/or sterilizable so as to facilitate easy and rapid conditioning for repeated reuse. It employs geometries and materials whose impedance characteristics, at typically used electrosurgical frequencies, are such that it self-limits current densities (and corresponding temperature rises) to safe thresholds, should the effective area of the working surface of the electrode be reduced below otherwise desirable levels. Accordingly, the need for the foregoing expensive monitoring circuits in specialized RF generators is eliminated. Furthermore, the improved return electrode incorporates a pressure sore pad that prevents the formation of pressure sores, while aiding with current transfer between the patient and the return electrode.

In accordance with a feature of the invention, an electrosurgical return electrode is made sufficiently large to present sufficiently low electrical impedance and low current densities at typical electrosurgery frequencies used in medical procedures to reduce the possibility of excessive temperature elevation in adjacent patient tissue, (i.e., by maintaining temperature ("T") rise below six degrees (6°) Celsius) thereby avoiding tissue necrosis or other undesired patient trauma.

In accordance with yet another feature of the invention, the working surface of the electrode (the electrode surface that is in contact with or in close proximity to the patient) is made sufficiently large in area so that in normal use, current flow will not be reduced to a point where it impedes the surgeon's ability to perform surgery at the surgical site.

In accordance with yet another feature of the invention, in one embodiment, the electrosurgical return electrode has a multi-layer construction, including an electrode and a pressure sore pad.

In accordance with yet another feature of the invention, in one embodiment, controlled electrical conductivity is imparted to the electrode by the inclusion therein of electrically conductive materials such as conductive threads or carbon black, thus conditioning conductivity as a function of surface area to levels which limit passage of current therethrough to safe values.

In accordance with yet another feature of the invention, in one embodiment, the electrosurgical return electrode includes a pressure sore pad with an integrally formed electrode coupled to the body of the pressure sore pad. As such, the material forming the pressure sore pad acts as, alternatively, a conductive layer or an insulative layer.

In accordance with yet another feature of the invention, the electrosurgical return electrode includes an interior material that is conductive while providing pressure relief to the patient.

In accordance with still another feature of the invention, the electrosurgical return electrode includes heating and cooling capabilities to either heat or cool a patient during a surgical procedure.

In accordance with another feature of the invention, the electrosurgical return electrode includes a pressure sore pad that provides heating and cooling capabilities to either heat or cool a patient during a surgical procedure, while the pad is self limiting and aids with the reduction in the creation of decubitus ulcers or pressure sores.

In accordance with yet another feature of the invention, in another embodiment, a moisture impervious working surface is provided for positioning adjacent an adjoining surface of the body of a patient, thus facilitating cleansing and reuse of the electrosurgical electrode.

In accordance with yet another feature of the invention, the aforementioned moisture impervious working surface is made resistant to normally encountered cleaning, disinfecting, and sterilizing agents, thus further facilitating cleansing and reuse.

In accordance with yet another feature of the invention, in another embodiment, a sleeve is provided for cooperative use with the electrosurgical electrode, thus protecting the electrode and the pressure sore pad from inadvertent damage that might occur, for example, from accidental contact of the active electrosurgical instrument with the electrode surface.

In accordance with yet another feature of the invention, the electrical impedance of the materials in and adjacent to the working surface of the electrode is sufficiently elevated so as to limit current density at the working surface to a level below the threshold of patient tissue trauma, thus providing a self-limiting characteristic to prevent patient trauma in the event of accidental reduction of the effective working surface of the electrode.

In accordance with yet another feature of the invention, in one embodiment, the electrosurgical electrode is form-fitted to the operating table on which the electrosurgical procedure is to be performed, thus facilitating realization of other features of the invention.

These and other objects and features of the present invention will become more fully apparent from the following description and appended claims, or may be learned by the practice of the invention as set forth hereinafter.

Additional features and advantages of the invention will be set forth in the description which follows, and in part will be obvious from the description, or may be learned by the practice of the invention. These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

To aid with understanding the various aspects and illustrative embodiments and features of the present invention, discussion will first be made with respect to the novel structures and features of a self-limiting electrosurgical electrode that may be used either on its own or in combination with a pressure sore pad. Following such a discussion, a detailed description of various illustrative embodiments of the novel pressure sore pad of the present invention will be described. The pressure sore pad having an electrosurgical electrode integrally formed therein allows one device to include both self-limiting characteristics necessary electrosurgical procedures, while incorporating the pressure reducing properties of a pressure sore pad that prevents the creation of pressure sores during various surgical procedures, including but not limited to electrosurgical procedures. In this manner, the novel electrosurgical electrodes of the present invention protect a patient from being burned during an electrosurgical procedures and stop pressure sores being created.

Figure 1:
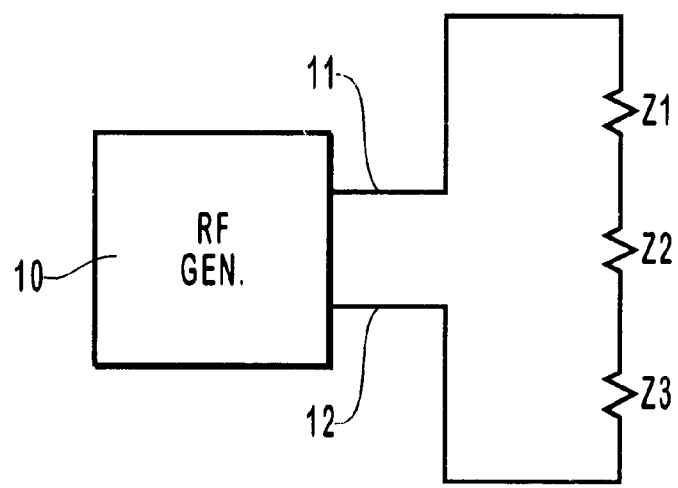
FIG. 1 is a simplified electrical schematic diagram illustrating typical impedances effectively included in the operative path of radio frequency current flow as presented to an electrosurgical generator during an operative procedure.

Now turning to the drawings, and more particularly FIG. 1 thereof, it will be seen to depict a simplified electrical schematic diagram illustrating typical impedances effectively included in the operative path of radio frequency current flow as presented to an electrosurgical generator during an operative procedure. There, it will be seen are conventional radio frequency electrical power generator 10, such as but not limited to constant power, voltage, and/or current or variable power, voltage and/or current. Connected to electrical power generator 10 are conventional electrical conductors 11 and 12 which respectively connect the generator 10 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 11 and 12 are representative of one illustrative structure that is capable of performing the function of connecting means for making electrical connection to the sheet. It may be appreciated by one skilled in the art, however, that various other structures are appropriate and capable of performing the desired function.

Although the diagram of FIG. 1 is simplified and generally considers circuit elements in terms of the principal resistances, including the reactants contributed by the surgical instrument, the patient's body and the return electrode, so as to clearly and succinctly illustrate principles of the invention, it should be understood that in reality certain other parameters would be encountered, parameters such as distributed inductance and distributed capacitance which, for purposes of clarity in illustration of the principles hereof, are deemed relatively small and so not considered at this point in this description. However, as set forth below, in one embodiment when an insulating sleeve is interposed between the electrode and the body of a patient, a significant element of capacitive reactance may be included in the impedance of $Z_3$. It should also be noted that FIGS. 1–10 are intentionally simplified so as to present the principles of the invention succinctly, with a more rigorous and complete discussion being presented in connection with FIGS. 11–17.

The initial embodiment, hereof, is that of an electrode operating in a combined resistive and/or capacitive mode. Accordingly, if the relatively small stray capacitive and inductive reactants are disregarded, the total effective impedance of the circuit will be equal to the sum of the individual impedances $z_1$, $z_2$ and $z_3$; and since essentially the same current will pass through all three, the voltage generated by RF generator 10 will be distributed across impedances $z_1$, $z_2$ and $z_3$ in direct proportion to their respective values. Thus, the energy released in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough (and consequent energy release) be concentrated in a very small region. The latter is accomplished by making the region of contact with the patient at the operative site very small.

It is known that, in contrast with the foregoing series circuit, components of combined resistive and capacitive reactance, when connected in parallel, present a total effective impedance that is given by the formula:

$$Z_{eff} = \frac{1}{\frac{1}{z_1} + \frac{1}{z_2} + \frac{1}{z_3} + \frac{1}{z_4} + \frac{1}{z_5} + \frac{1}{z_6}} \tag{1}$$

Thus, if 100 similar impedances, each of 100 ohms, were connected in parallel, the effective impedance $Z_{eff}$ would equal one ohm. If half of such impedances were effectively disconnected, the remaining effective impedance would be two ohms, and if only one of the impedances were active in the circuit, the remaining effective impedance would be 100 ohms. The significance of these considerations and their employment to render the electrode hereof self-limiting and fail-safe will be evident from the following description of the elements illustrated in FIGS. 2A, 2B, 2C and 3.

Figure 2A:
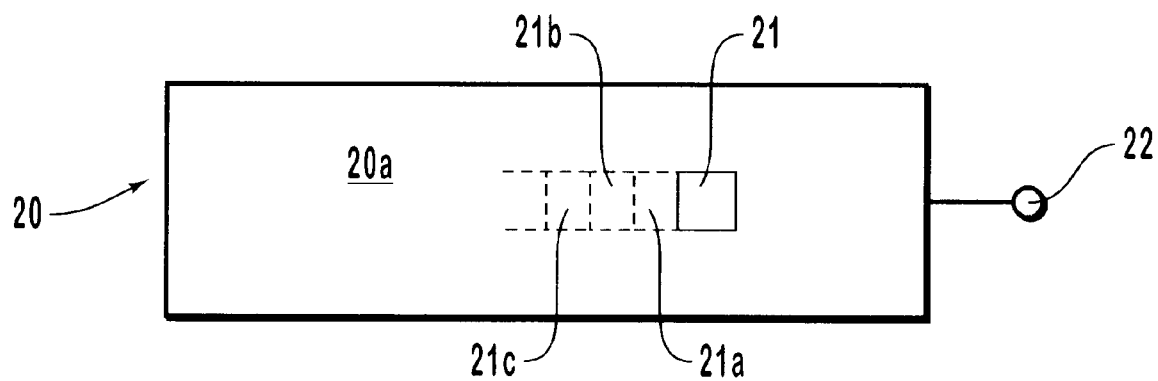
FIG. 2A is a top view of a wide-area distributed electrosurgical return electrode illustrating the principles of the invention.

Now turning to FIG. 2A, there will be seen a schematic representation of the top view of a wide-area distributed electrosurgical return electrode 20 illustrating the principles of the invention. At the right hand side of the figure there is shown an electrical connection terminal 22 to facilitate connection to an electrical return conductor, such as conductor 12 of FIG. 1.

Figure 2B:
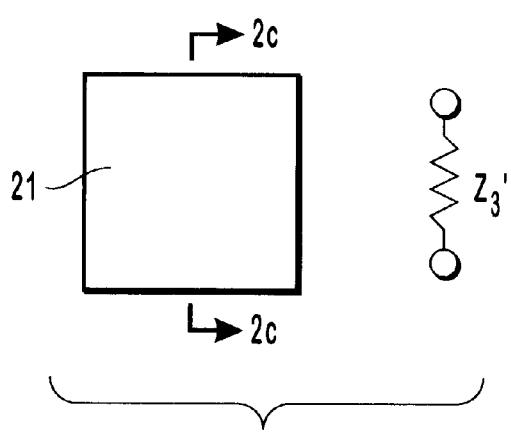
FIG. 2B is an enlargement of a segment of the electrosurgical return electrode of FIG. 2A.
Figure 2C:
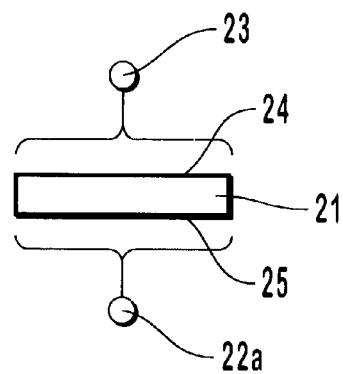
FIG. 2C is a cross section taken along the section lines 2C—2C of FIG. 2B and illustrating the effective circuit impedance represented by the segment of 2B.

The surface 20a of return electrode 20 is preferably smooth and homogeneous and includes a thin resistive and/or dielectric layer 21a (FIG. 2C). Alternatively, surface 20a of return electrode 20 may include a capacitive and/or inductive layer, depending on the particular operation of return electrode 20. For instructional purposes of this description and to aid in the mathematical modeling of return electrode 20, electrode 20 may be thought of as including a plurality of uniformly-sized regions or segments as represented by regions 21, 21a, 21b, 21c . . . 21n. It will be appreciated by one skilled in the art, however, that return electrode may or may not include discontinuous regions or segment, it being preferred that electrode 20 have continuous segments.

Region/segment 21 is shown larger in FIG. 2B in order to be similar in scale to the resistive impedance $z_3'$ it represents. It thus will now be evident that each of the segments of electrode 20 corresponding to segments 21 . . . 21n inherently has the capability of presenting an impedance similar to that of impedance $z_3'$. However, the number of such segments which are effectively active in parallel within the circuit is a direct function of the surface area of the patient that overlies the electrode. Thus, in the case of a large supine patient whose body is in effective contact with 50 percent (50%) of the upper surface of the electrode, 50 percent of the segments corresponding to segments 21–21n will be effectively paralleled in the circuit to form an impedance represented by impedance $z_3$ of FIG. 1; and, accordingly, if electrode 20 contains 100 segments of 100 ohms each, the effective impedance operatively presented by the effective 50 percent of the electrode elements would be 2 ohms. Since 2 ohms is very small compared with the impedance represented by elements $z_1$ and $z_2'$, very little energy is lost at the region of contact between the patient and the electrode, and due also to the relatively large effective working area of the electrode, current density, and temperature elevation are maintained below the danger thresholds mentioned above.

Now, if for any reason, the effective contact area between the patient and electrode were to be reduced to the surface of only one of the segments 21–21n, then the effective impedance (combined capacitive reactance and resistance in the example under consideration) would increase to 100 ohms; and at some point of reduction in contact area, the effective impedance would rise to a level relative to the impedance presented at the site of the electrosurgical instrument so as to diminish the electrosurgical effect of the surgical instrument or otherwise prevent effective use of the instrument by the surgeon, thus signaling the surgeon that the patient should be repositioned so as to present a greater surface area in contact with the return electrode. At the same time, the total circuit impedance would be increased so that the total current that would flow if the surgeon attempted to employ his instrument without repositioning the patient would be reduced to a value below that which would cause undesired trauma to the patient. Accordingly, there is provided a self-limiting feature that enhances safety in use without the need for the aforementioned separate circuit monitoring and control circuits.

FIG. 2C is a cross section taken along the section lines 2C—2C of FIG. 2B and illustrates the effective circuit impedance $z_3'$ represented by the segment 21 of 2B. There, in FIG. 2C are seen small segment 21 with its upper patient-contacting surface 24 represented electrically by terminal 23 and its lower surface 25 represented by electrical terminal 22a. For the purpose of this description (and in order to present the principles underlying this embodiment clearly), the impedance $z_3'$ may be thought of as existing between terminals 23 and 22a. Of course, it will be evident to those skilled in the art that in an embodiment in which a thin but highly conductive layer is included along the lower surface of electrode 20, each of the impedances represented by the remaining segments are connected at their lower extremities in parallel to terminal 22; whereas, if such highly conductive layer is absent, then, in addition to the impedance represented by the material lying between the upper and lower regions of each segment, there will be an additional impedance (not shown) that is represented by the material through which current would have to pass transversely or laterally through the electrode in order to get to terminal 22.

It should now be evident that if lateral impedance is minimized by provision of the aforementioned thin conducting layer, or if the effective conductivity at the lower part of the material of region 21 is otherwise increased, the effective impedance presented by the return electrode will be inversely proportional to the effective upper surface of the electrode that is in contact with a patient.

Figure 3:
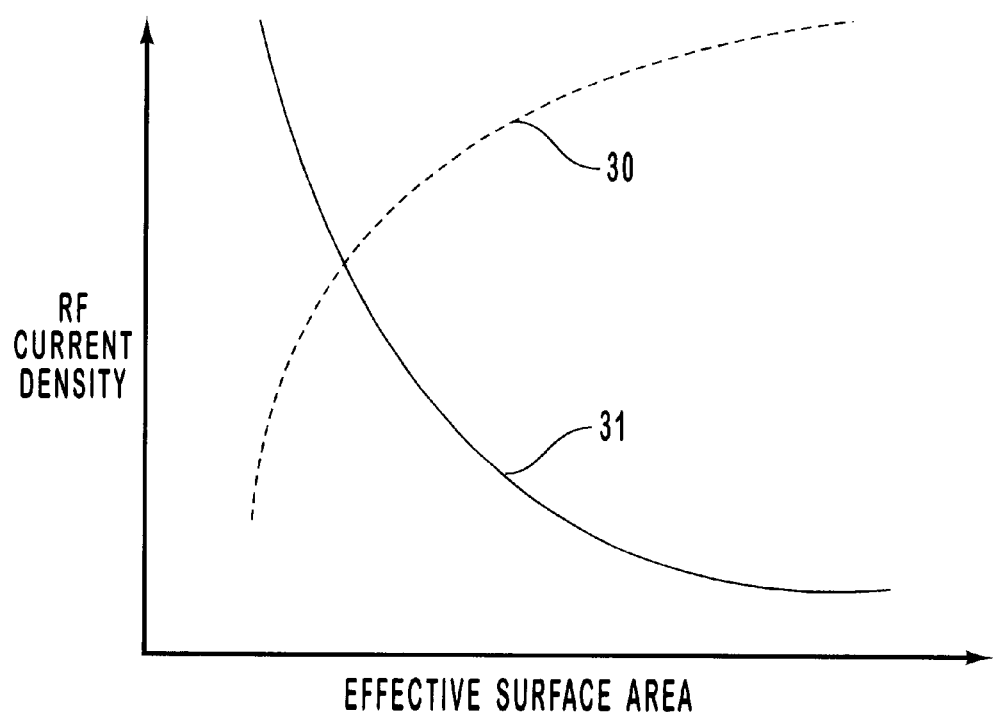
FIG. 3 is a chart illustrating in graphical form the relationships between effective surface area of the return electrode and the effective radio frequency current density developed at the electrode.

FIG. 3 is a chart generally illustrating in graphic form the relationships between the effective surface area of the return electrode and the effective radio frequency current densities developed at the electrode. However, before proceeding to a consideration of such chart, it should be noted that the chart is simplified so as to illustrate the principles underlying the invention and does not represent actual data that may vary substantially. In FIG. 3 there is seen a plot of RF Current Density versus Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 30) and the corresponding current density across the return electrode is very low (solid graph line 31). This is, of course, the condition desired for conducting surgery. However, if we assume constant current throughout the circuit, as the effective surface area decreases, the current density across the return electrode (solid graph line 31) increases with a corresponding decrease in the current at the surgeon's instrument (dashed graph line 30). When the effective surface area declines to some predetermined point, there will remain insufficient current at the surgical instrument to effectively conduct surgery.

It may be appreciated by one skilled in the art that the change in current density and available current to the surgeon may or may not occur simultaneously with the variations in effective surface area. Various embodiments of the present invention may have substantially simultaneous changes in current density and available current, while other embodiments of the present invention may include a lag period therebetween.

The parameters selected for the materials and electrode dimensions are chosen so that current density and corresponding tissue temperature elevation adjacent the return electrode do not exceed the limits mentioned in the introduction hereof. It will now be seen that by a proper selection of such parameters the return electrode is made self-limiting, thereby obviating the need for the additional monitoring circuits to which reference is made above.

To facilitate description of the principles underlying the invention, the foregoing is described in terms of impedances whose principal components are resistances and capacitive reactants. However, the principles of the invention are also applicable to other embodiments in which the impedances include any combination of resistive, capacitive and/or inductive impedances.

The invention hereof is now further described in connection with applications in which an effective dielectric layer is represented by a physical dielectric layer on the upper surface of the electrode, by the material of a surgical gown worn by the patient, by a bed sheet or other operating room linens interposed between the patient and the return electrode, by the material of a protective sleeve fitted over the return electrode, or any combination thereof.

Figure 4:
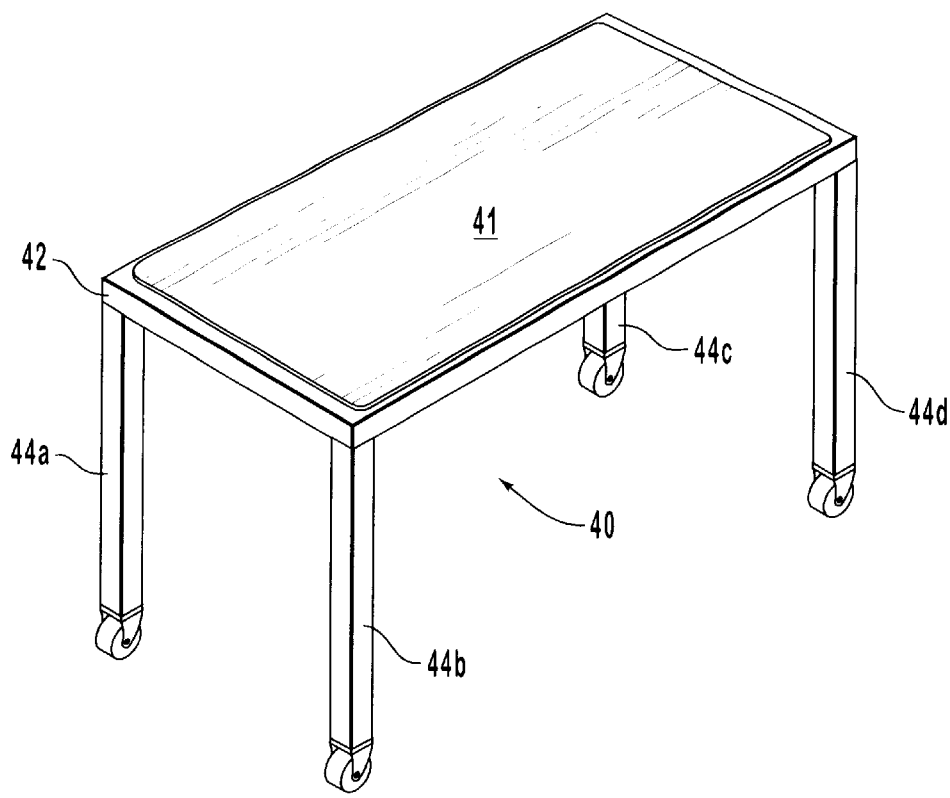
FIG. 4 is a perspective view showing an operating table with the electrosurgical return electrode according to the invention disposed on the upper surface thereof.

Reference is now made to FIG. 4, which illustrates in perspective an operating table 40 with an electrosurgical return electrode 41 according to the invention disposed on the upper surface thereof, an edge of which is identified by the numerals 42. The operating table is shown to have conventional legs 44a–44d that may be fitted with wheels or rollers as shown. Table 40 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Figure 5:
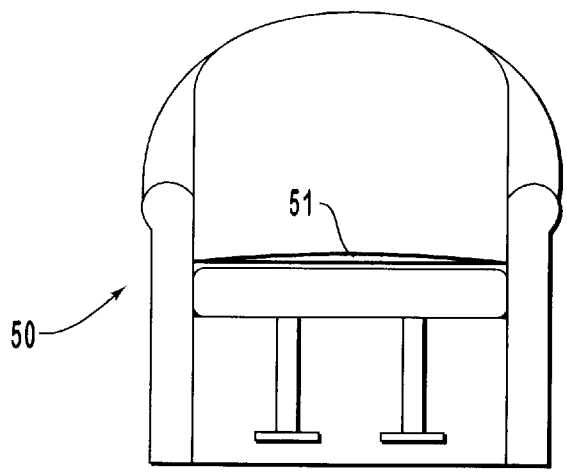
FIG. 5 is a front view illustrating a surgical chair with an electrosurgical return electrode according to the invention disposed on the surface of the seat thereof.

Although in FIG. 4, the entire upper surface of the table is shown as being covered with return electrode 41, it should be understood that entire coverage is by no means required in order to practice the principles of the invention. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-half of the torso for an adult patient lying on an operating table or the buttocks of a patient sitting in a chair such as is illustrated in FIG. 5. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although the return electrodes shown in FIGS. 6–8, and 10 are depicted as being rectangular in shape, it will be evident that they could be oval or contoured as, for example, to follow the silhouette of the torso or other principal part of the body of a patient. As will be evident from the foregoing, it is important that the electrode be configured so that when the electrode is used: (1) the return current density on the surface of the patient is sufficiently low; (2) the electrical impedance between the electrode and the patient is sufficiently low so that electrical energy is not concentrated sufficiently to heat the skin of the patient at any location in the electrical return path by more than six degrees (6°) Celsius; and (3) the characteristics of the materials and geometries are such that if the effective area of the electrode is reduced below a selected threshold level, there will be insufficient energy dissipated at the surgeon's implement for him to continue effectively using the implement in its electrosurgical mode.

As will be recognized by those skilled in the art, it is not necessary for there to be direct ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$.

As is known to those skilled in the art, in an alternating current circuit (e.g., such as those used in electrosurgery) the capacitive reactance of an impedance is a function both of capacitance and the frequency of the alternating current electrical signal presented to the reactance. Thus, the formula for capacitive reactance (in ohms) is $$Xc = \frac{1}{2\pi fC} \tag{2}$$

where Xc is capacitive reactance in ohms ($\pi$) is 3.14159, f is frequency in hertz, and C is capacitance in farads.

The formula for capacitance in a parallel plate capacitor is:

$$C = \frac{\kappa \varepsilon_0 A}{t} \tag{3}$$

where C is capacitance in Farads, $\kappa$ is the dielectric constant of the material lying between the effective plates of the capacitor, A is the area of the smallest one of the effective plates of the capacitor in square meters, t is separation of the surfaces of the effective plates in meters, and $\varepsilon_0$ is the permittivity of air in Farads/meter. Thus, it will be seen that to meet maximum permissible temperature rise criteria in an embodiment in which electrode circuit capacitance is substantial, different minimum sizes of electrodes may be required depending upon the frequency of the electrical generator source, the separation of the body of the patient from the electrode, and the material lying between the effective conductive region of the electrode and the adjacent body surface. Accordingly, although the principles of the invention are applicable to a wide range of frequencies of electrosurgical energy, the considerations set forth herein for minimum sizes of return electrodes specifically contemplate frequencies typically employed in conventional electrosurgical energy generators.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the invention hereof, would need a minimum effective area of between about 7 and about 11 square inches (about 45 $cm^2$ to about 70 $cm^2$) with a relatively small separation from the skin of the patient such as that provided by a surgical gown or no interposing gown at all. Such an effective area is easy to obtain if the patient is positioned on an electrode that is the size of their upper torso or larger.

The characteristics of the desired dielectric for the present embodiment are sufficiently comparable to those of selected rubbers, plastics and other related materials that the latter may be satisfactorily employed as materials for the return electrode. As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

As mentioned above, FIG. 5 is a front view illustrating a surgical chair 50 with an electrosurgical return electrode 51 according to the invention disposed on the upper surface of the seat thereof. Accordingly, when a patient is sitting in the chair, the buttocks and upper part of the thighs overlie and are in sufficiently close proximity to the return electrode so that coupling there between presents an impedance meeting the foregoing criteria; namely, that the electrical impedance between it and the patient is sufficiently low to allow the surgeon to perform the procedure while providing that current density is sufficiently low and that insufficient electrical energy is developed across the return impedance to heat the skin of the patient at any location in the electrical return path by more than six degrees (6°) Celsius.

Figure 6:
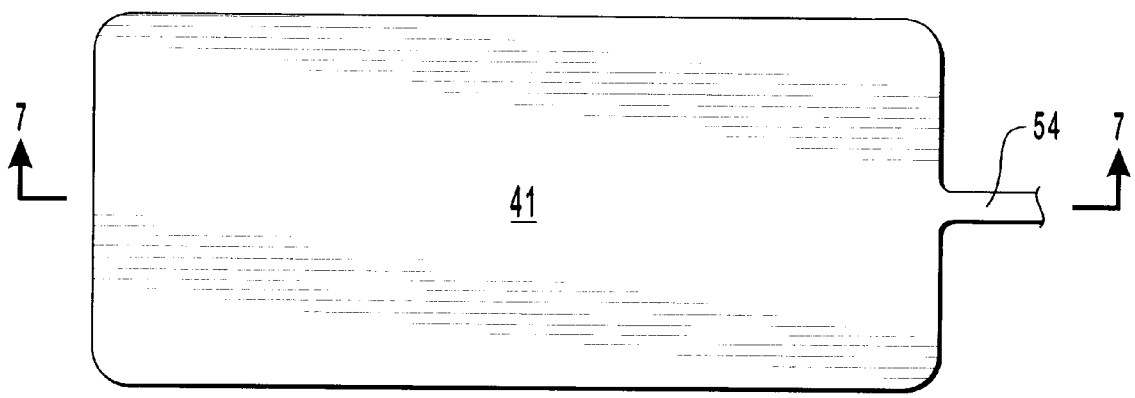
FIG. 6 is a top view of an electrosurgical return electrode according to the invention.

FIG. 6 is a top view of another electrosurgical return electrode according to the invention. It will be observed that the upper exposed, or working, surface of the electrode again is expansive so as to meet the foregoing criteria for low impedance. Although it is not necessary that the electrode cover the entire surface of an operating table or the entire seat surface of a dental or other patient chair, it has been found advantageous in some instances to provide a greater surface area than that of the projected area of the buttocks or torso of a patient so that if a patient moves position during the course of a procedure, a sufficient portion of the patient will remain in registration with the electrode surface so that the effective impedance will remain less than the above-described level.

At this juncture, it may be helpful to emphasize characteristics of the improved electrode according to the invention hereof that are deemed particularly relevant to an understanding of the inventive character thereof. First, as mentioned above, the electrode does not need to be in direct contact with a patient, either directly or through intervening conductive or nonconductive gel. In addition, because of its expansive size, there is no need for tailoring the electrode to fit physical contours of a patient. In this connection, it has been found that although with selected materials and geometries, the self-correcting and self-limiting principles hereof could be achieved in an electrode as small as about seven square inches (or about 45 square centimeters) in working surface area, the preferable range of exposed upper working surface area of the electrode lies in the range of from about 11 to 1,500 square inches (or about 70 to 9,680 square centimeters). By making the electrode several times larger (typically, at least an order of magnitude larger) in working surface area than previous proposals, the need for direct physical attachment, either directly to the skin of the patient or through gels, is eliminated.

The electrode according to the invention hereof, as illustrated in FIG. 6, may be made of conductive plastic, rubber, or other flexible material which, when employed in the electrode will result in an effective dc resistance presented by each square centimeter of working surface to be greater than about 8000 Ω. Silicone or butyl rubber has been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Further reference to FIG. 6 reveals the presence of a conventional electrical connector 54 attached to the electrode 41 to provide a conventional electrical return to the electrosurgical radio frequency energy source (not shown). Connector 54 is another structure capable of performing the function of connecting means for making electrical connection to the sheet. Connector 54 is only illustrative of one possible structure for performing the desired function; it being appreciated by one skilled in the art that various other structures are capable of performing the required function.

Figure 7:
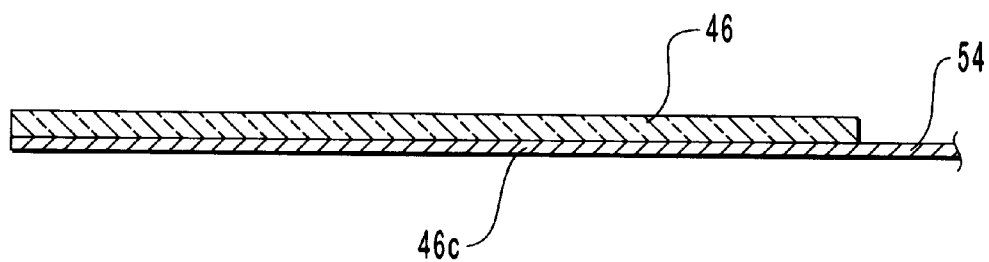
FIG. 7 is a section taken along the lines 7—7 of FIG. 6.

As mentioned above, FIG. 7 is a section taken along the lines 7—7 of FIG. 6. FIG. 7 shows an electrode 46 similar to electrode 20 of FIGS. 2A–2C, except that electrode 46 includes a thin highly conductive lower stratum 46c to facilitate conduction of current outwardly to terminal 54. In one preferred form, the thickness of the electrode lies in a range from about 1/32 inch to 1/4 inch (about 0.08 cm to 0.64 cm), which, with the aforementioned range of impedance of the main body of material and the capacitive reactance of the upper dielectric layer, provides the required impedance together with desired physical flexibility for ease of use and handling.

Figure 8:
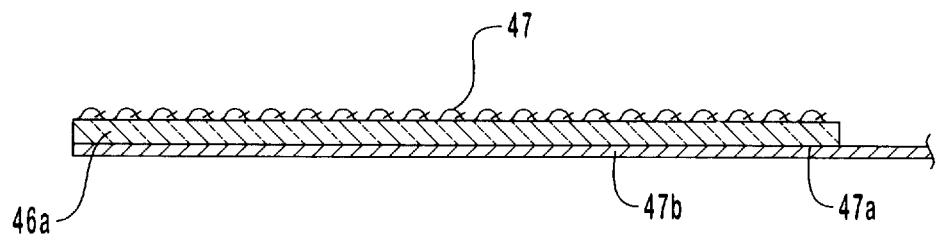
FIG. 8 is a section similar to that of FIG. 7 but illustrating the capacitance presented by a patient's surgical gown.

FIG. 8 is a section similar to that of FIG. 7, but presenting a multiple layer embodiment illustrating the separation presented by a patient's gown according to the invention hereof. There, in FIG. 8 are shown a layer 46a (similar to layer 46 of FIG. 7) and an overlying effectively capacitive layer 47 representing an insulating dielectric layer, a patient's surgical gown, an operating room linen, a protective sleeve or sheath, or any combination thereof. It should be understood that in addition to a construction similar to that of the electrode of FIGS. 6–7, a conductive layer 47a of FIG. 8 could comprise a sheet or screen of gold, brass, aluminum, copper, silver, nickel, steel, stainless steel, conductive carbon, conductive fluids, gels, saline, and the like. Further reference to FIG. 8 reveals another dielectric layer 47b covering the lower surfaces of layer 46a.

Figure 9:
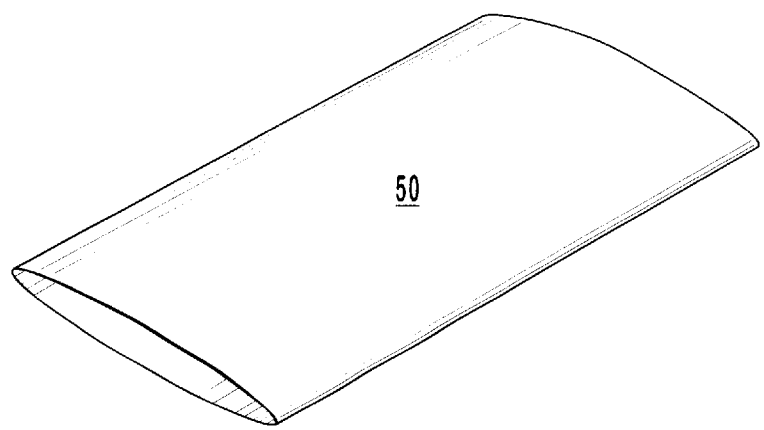
FIG. 9 is a perspective view of a cover adapted for encasing any of the embodiments of FIGS. 6–8.

FIG. 9 is a perspective view of a sleeve 50 adapted for encasing any one of the embodiments of FIGS. 6–8. Thus, provision is optionally made for encasing the foregoing return electrode-shaped electrodes within protective envelopes in situations in which it is desired to eliminate the need for cleaning the electrode itself by protecting it from contamination through the use of a sleeve of impervious material from which the electrode, after use, can merely be withdrawn and the sleeve discarded. As will be evident to those skilled in the art, such a sleeve may preferably be made of any of a variety of known materials, such as vinyl plastics, polyester or polyethylene.

Figure 10:
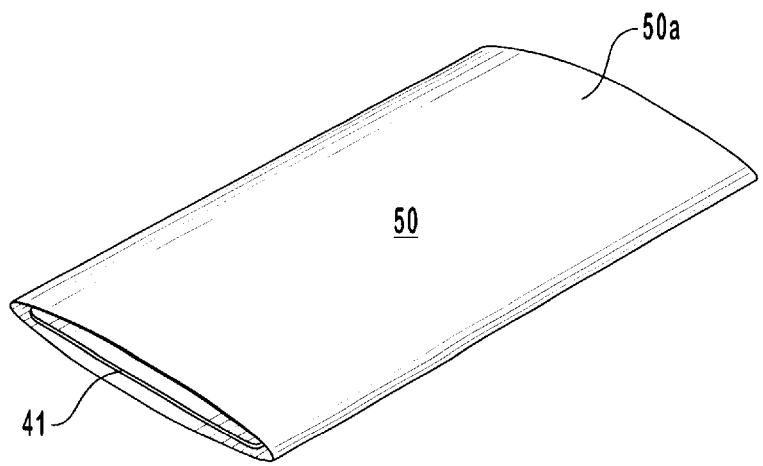
FIG. 10 is a view illustrating one of the embodiments of FIGS. 6–8 encased within the cover of FIG. 9.

FIG. 10 is a view illustrating one of the embodiments of FIGS. 6–8 encased within the sleeve of FIG. 9. There, it will be seen, is outer surface 50a of sleeve 50; and shown encased within sleeve 50 for illustrative purposes is electrode 41 of FIG. 6.

Total Electrode Ground Pad Impedance and Self-Limiting Feature

Figure 11:
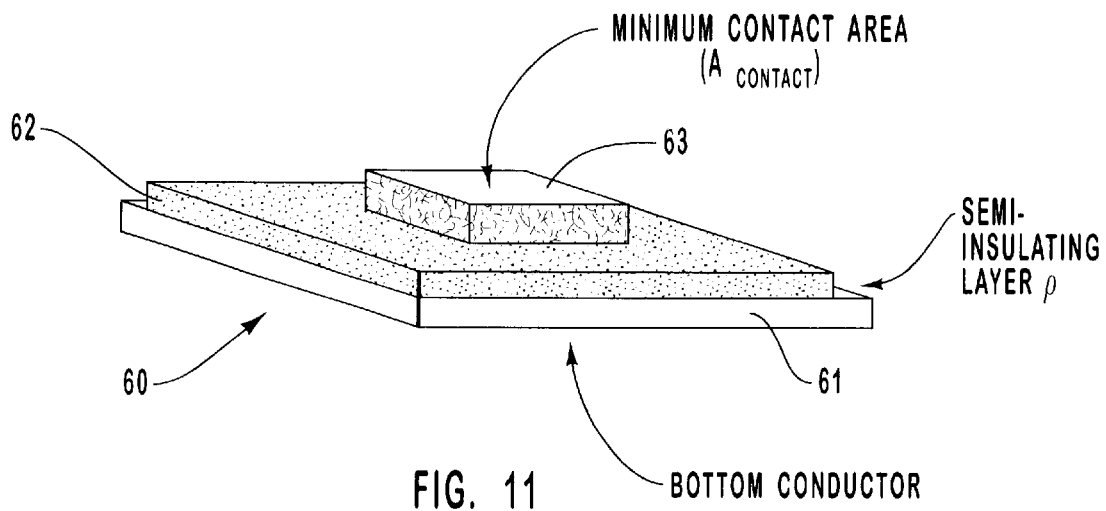
FIG. 11 is a perspective view of an electrode according to the invention illustrating a simulated condition when the effective contact area with a patient is substantially less than the physical electrode size.

FIG. 11 depicts an electrosurgical electrode 60 consisting of a conductive metal backing 61 and a semi-insulating layer 62. The electrode 60, and more specifically, semi-insulating layer 62, is in contact with another conducting layer 63 which represents a patient thereupon. The self-limiting feature of electrosurgical return electrode 60 (maintains current densities below a threshold level) arises due to the total impedance of electrode 60, whether such impedance arises from semi-insulating layer 62 alone or in combination with conductive metal backing 61 and/or conducting layer 63. Furthermore, the total impedance may arise from the various resistive, inductive, and/or capacitive components of conductive metal backing 61, semi-insulating layer 62 and/or conducting layer 63.

Electrode 60, which includes a single layer of semi-insulative material 62 having a bulk resistivity ρ and thickness t. An area A placed between a conductive surface and the patient may be modeled as a resistor (R) in parallel with a capacitor (C).

For ease of explanation, we will determine the resistive requirements of electrode 60 for self-limiting in a purely resistive scenario where electrode 60 is modeled as a resistor in parallel with a capacitor. Following the calculation of the minimum requirements for self-limiting in the purely resistive case, we will generalize the analysis for any impedances, whether such impedances result from resistive, capacitive, and/or inductive components.

As such, the resultant total impedance equivalent for the resistor in parallel with the capacitor combination is $$Z_{tot} = R \| X_c = \frac{(R)\left(\frac{1}{j\omega C}\right)}{(R) + \left(\frac{1}{j\omega C}\right)} = \frac{R}{1 + j\omega CR} \quad (4)$$

where j is an imaginary component of reactance, and ω is the angular frequency and is defined as $\omega = 2\pi f$ where f is the electrosurgical generator frequency. The magnitude of the impedance is $$|Z_{tot}| = \sqrt{\frac{R^2}{1 + \omega^2 C^2 R^2}} = R\sqrt{\frac{1}{1 + \omega^2 C^2 R^2}} \quad (5)$$

Substituting the dependence of R and C on the area A, thickness t, bulk resistivity ρ, and the dielectric constant of the material κ defined by $$R = \frac{\rho t}{A} \quad (6)$$

and $$C = \frac{\kappa \varepsilon_0 A}{t} \quad (7)$$

where permittivity constant $\epsilon_0 = 8.85 \times 10^{-12}$ F/m, the magnitude of the total impedance is given by $$|Z_{tot}| = \frac{\rho t}{A}\sqrt{\frac{1}{1 + \omega^2\left(\frac{\kappa \varepsilon_0 A}{t}\right)^2\left(\frac{\rho t}{A}\right)^2}} = \frac{\rho t}{A}\sqrt{\frac{1}{1 + \omega^2\kappa^2\varepsilon_0^2\rho^2}} \quad (8)$$

According to the AAMI standard, the total impedance of the electrosurgical electrode should be less than 75 Ω under normal operating conditions. It is preferred, therefore, that $$\frac{\rho t}{A}\sqrt{\frac{1}{1 + \omega^2\kappa^2\varepsilon_0^2\rho^2}} \leq 75\Omega \quad (9)$$

We define β as $$\beta = \frac{Z_{tot}}{75\Omega} \quad (10)$$

If β<<1, the electrode will have very low impedance compared to the AAMI standard, and the surgeon will not notice any degradation in the electrosurgical cutting power due to the electrode. If β>>1, the electrosurgical electrode will have such a large impedance that the surgeon will no longer be able to perform electrosurgery. Using β in the above inequality, the expression becomes an equality:

$$\frac{\rho t}{A}\sqrt{\frac{1}{1 + \omega^2\kappa^2\varepsilon_0^2\rho^2}} = 75\beta \quad (11)$$

It is preferred that self-limiting occurs when the electrode has a large electrode area in contact with the patient (FIG. 15); however it is also necessary for self-limiting to occur when the patient only makes contact with a small fraction of the total electrode area (FIG. 11). For self-limiting to work properly, it is necessary for the current density (I/A), where I is the total current through the contact area A of the electrosurgical return electrode, to not exceed a critical value $$\left(\frac{I}{A}\right) \leq \left(\frac{I}{A}\right)_{critical} = 100 \text{ mA/cm}^2 \quad (12)$$

AAMI standards indicate that normal electrosurgical currents are on the order of 500–700 mA. If we set 1000 mA=$I_{max}$ as a safe upper limit as to what one might expect for an above average power surgery, then, in order to return the current to the electrode without exceeding $I_{critical}$, the contact area $A_{contact(min)}$ for traditional electrosurgical return electrodes must have a minimum size:

$$A_{contact(min)} \geq \frac{I_{max}}{\left(\frac{I}{A}\right)_{critical}} = \frac{1000 \text{ mA}}{100 \text{ mA/cm}^2} = 10 \text{ cm}^2 \quad (13)$$

It can be appreciated that $I_{max}$ may vary from patient to patient due to changes in the amount of time that the electrode is in contact with the patient, the electrical characteristics of the patient's skin (i.e., resistivity, and the like), the amount of heat being conducted by the patient, the patient's initial skin temperature, and the like. With an electrosurgical return electrode designed according to the prior art, in the event that the contact area with the patient reduces below the $A_{contact(min)}$, while maintaining the $I_{max}$, a burn may result because $(I/A)_{critical}$>100 mA/cm², which is the burn threshold. In contrast, the present invention limits the possibility of a burn caused from a reduction of the contact area below $A_{contact(min)}$, while also preventing electrosurgical procedures when the contact area is significantly 22 reduced. Therefore, by selecting the appropriate impedance of electrode 60, the current I is always reduced below $I_{max}$ when A<$A_{contact(min)}$.

Figure 12:
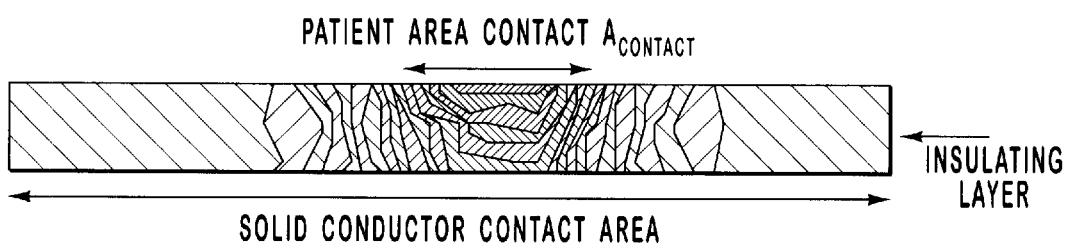
FIG. 12 is a view illustrating current flow density within the electrode when the effective patient contact area is much smaller than the total electrode area.

As such, the impedance between the small electrode with area $A_{contact(min)}$ and the larger metal foil is not simply $$R = \frac{\rho t}{A_{contact\,(min)}} \tag{14}$$

as current can flow through the areas not directly below the patient contact area $A_{contact(min)}$ (FIG. 12). Approximately 10–20% more current flows through the patient contact area $A_{contact}$ than one would expect if the total area of the insulative layer were $A_{contact(min)}$. Equivalently, the effective impedance of the electrode is 10–20% less than what one would normally expect if these edge effects were not present resulting in additional current flow.

As previously mentioned, FIG. 12 reveals current flow distribution through the semi-insulating part of the electrode when the upper contact area with the patient is much smaller than the total electrode surface area. As depicted, current flows through parallel paths around the contact region thus reducing the overall impedance to current flow and thereby increasing the effective area about 10–20 percent. In the Figure, the opaque or heavily hatched region denotes heavier current flow, and the lighter or lightly hatched region denotes lesser current flow.

In order for the electrode to be self limiting, and is efficacious as defined by the AAMI standard, it is preferred that $A_{contact(min)}$ have a value from about 7 cm² to about 22 cm², and more preferably about 10 cm² for electrosurgical currents between 100 mA and about 2,000 mA. Similarly, it is preferred that β range from about 10 to about 50, and more preferably have a value of about 10. Using the various values for $A_{contact(min)}$ and β, it is preferable to solve Equation 11 for the thickness t as a function of the bulk resistivity ρ at different electrosurgical generator frequencies ω, while inserting a factor of 1.2 to account for the edge effects described above. In the particular illustrative embodiment discussed herein, the factor of 1.2 is included within the resistivity and reactance terms of the equation; however, it may be appreciated by one skilled in the art that the factor of 1.2 is geometry dependent for both the resistive and reactance terms and may vary. Additionally, the value of 1.2 is based on the illustrative geometry of the presently described self-limiting electrode and may vary as the geometry of the electrode varies to account for the different edge effects.

The resulting equation (which identifies and defines the interrelationships of parameters affecting self-limitation) is $$t = \frac{1.2A(75\beta)\sqrt{1+\omega^2\rho^2\kappa^2\varepsilon_0^2}}{\rho} \tag{15}$$

Figure 13:
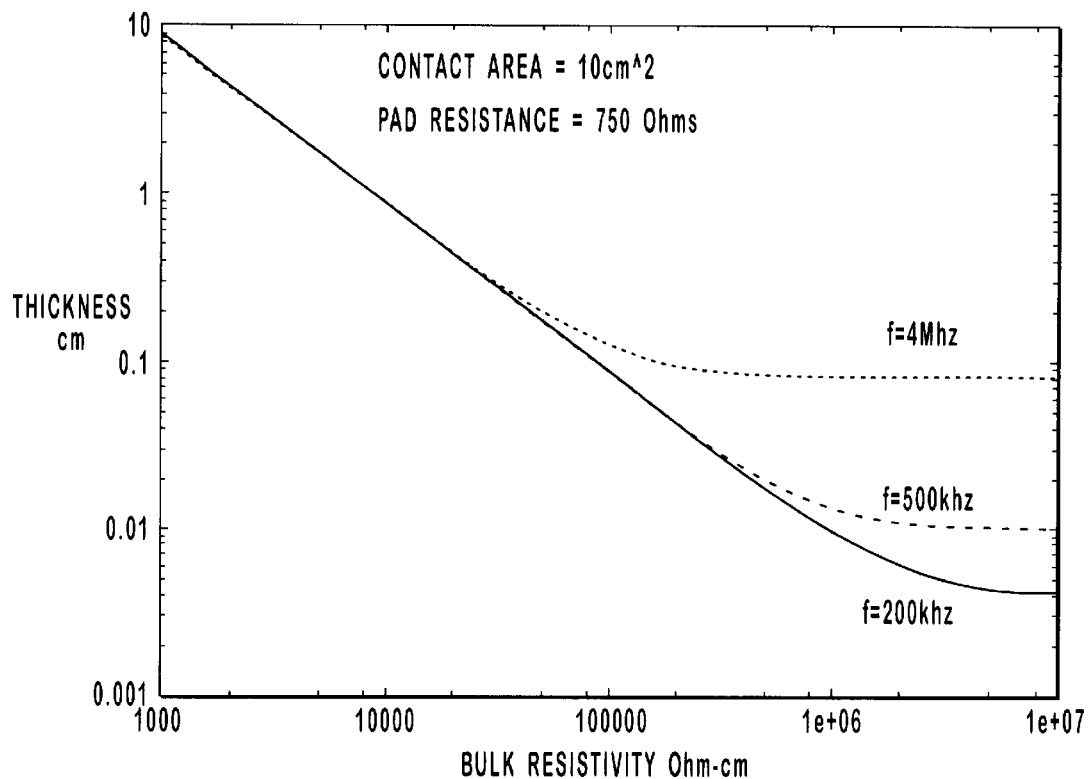
FIG. 13 is a graph depicting variations of bulk resistivity of the resistive layer as a function of electrode thickness for different electrosurgical generator frequencies.

Using Equation 15, FIG. 13 illustrates the variation of minimum bulk resistivity, with electrode thickness, requiring κ=5. The maximum electrode thickness one could imagine using would range from about 0.5 to about 4 inches (about 1.3 cm to about 10.2 cm) and more preferably about 1 inch thick (about 2.5 cm). Above these thicknesses, the electrode may become unwieldy to use and uncomfortable for the patient. Thus, to be self-limiting, the minimum bulk resistivity for an electrode of such thickness is about 4000 Ω·cm.

The preceding equations and discussion are representative of the bulk resistivity required for electrode 60 (FIG. 11) to be self-limiting. It may be appreciated, however, that the above analysis may be repeated to obtain the necessary self-limiting impedances for electrodes modeled using primarily capacitive or inductive components, or combinations of resistive, capacitive, and/or inductive components. Therefore, following is a discussion of the self-limiting requirements for the bulk impedance of electrode 60, whether such impedance arises from resistive, capacitive, and/or inductive components of impedance.

The self-limiting behavior of the electrosurgical electrode of the present invention results from the existence of sufficient return impedance to make an electrode site burn impossible when the area of contact between the patient and the electrosurgical return electrode is substantially reduced. As shown above, the combination of the maximum electrosurgical currents of 1000 mA coupled with the requirement that the current density be kept below 100 mA/cm² yields a minimum safe contact area of 10 cm².

In general, this requirement can be met with any number of electronic components hooked together in various configurations, including series and parallel combinations of capacitors, resistors, and even inductors, provided that the total impedance presented by the resulting circuit be about 75β or greater when the contact area is reduced to 10 cm².

Define the total impedance of the circuit between the return electrode of the electrosurgical generator and the patient as $Z_{TOT}$. This impedance is generated by the capacitive, resistive, and inductive properties of the materials inserted between the patient and the return electrode. We define the "bulk impedance" of the material η, a volume independent measure of the impedance of the material, that is frequency dependent, as:

$$\eta = \frac{(A)(Z_{TOT})}{t} \tag{16}$$

Here A is the area of the material and t is the thickness. This is analogous to the relationship between the volume dependent ohmic resistance R and the related volume independent characteristic of the resistive material called the "bulk resistivity" ρ described earlier.

One manner to describe the self-limiting requirement is expressed in terms of η:

$$|Z_{TOT}| = \frac{t|\eta|}{A} > 75\beta \tag{17}$$

Or therefore $$|\eta| > \frac{(75\,\beta)A}{t} \tag{18}$$

For the previous case (minimum bulk resistivity specification) we used $A=A_{contact(min)}=10$ cm², (about 1.55 inch²), β=10, and t=$t_{max}$=1 inch (about 2.5 cm), and a factor of 1.2 to account for edge effects to find that for a pure resistive electrosurgical electrode, $$|\eta|>4000\;\Omega\cdot cm \tag{19}$$

Therefore, in the purely resistive case, the bulk impedance (η) is identified as the bulk resistivity (ρ) of the conducting material in the electrode. The results in Equation 19, however, generalize to all materials and electrical components, including resistive, capacitive, and inductive components, and any combinations thereof. As long as the bulk impedance of the electrosurgical electrode is greater than 4000 Ω·cm, the electrode will be self-limiting, regardless of whether the self-limiting behavior is due to a resistive, capacitive, inductive impedance, or any combination of these impedances.

As alternate illustrative examples, one might construct a self-limiting electrosurgical electrode using a conductive/ resistive return plate coated with an insulating (dielectric) material or one might construct a patient gown out of dielectric material and use a metallic or resistive return electrode. The total effect of these devices would be to create a resistive impedance in series with a capacitive impedance.

For the above defined illustrative examples that model the return electrode in terms of resistive and capacitive impedances, the total impedance of the electrosurgical electrode is the sum of the resistive and the capacitive impedances:

$$Z_{TOT} = R + \frac{1}{j\omega C} \tag{20}$$

In terms of the material bulk resistivity, dielectric constant, area, and thickness, the total impedance is:

$$Z_{TOT} = \frac{\rho t}{A} + \frac{t}{j\omega \kappa \varepsilon_0 A} \tag{21}$$

By multiplying both sides of the equation by the area A, and dividing by the thickness t, we can derive the bulk impedance $\eta$:

$$\eta = \rho + \frac{1}{j\omega \kappa \varepsilon_0} \tag{22}$$

The magnitude of the bulk impedance is:

$$|\eta| = \sqrt{\rho^2 + \frac{1}{(\omega \kappa \varepsilon_0)^2}} \tag{23}$$

If we require $$|\eta| > \frac{(75\,\beta)(1.2A)}{t} \tag{24}$$

Then $$\frac{A}{t} < \frac{|\eta|}{1.2(75\,\beta)} = \frac{\sqrt{\rho^2 + \frac{1}{(\omega \kappa \varepsilon_0)^2}}}{1.2(75\,\beta)} \tag{25}$$

As such, the edge effects reduce the bulk impedance of the electrode by about 10–20 percent, thereby causing a corresponding increase in the effective area of the self-limiting electrode by about 10–20 percent and reduces the possibility of unwanted electrosurgical burns.

Figure 14:
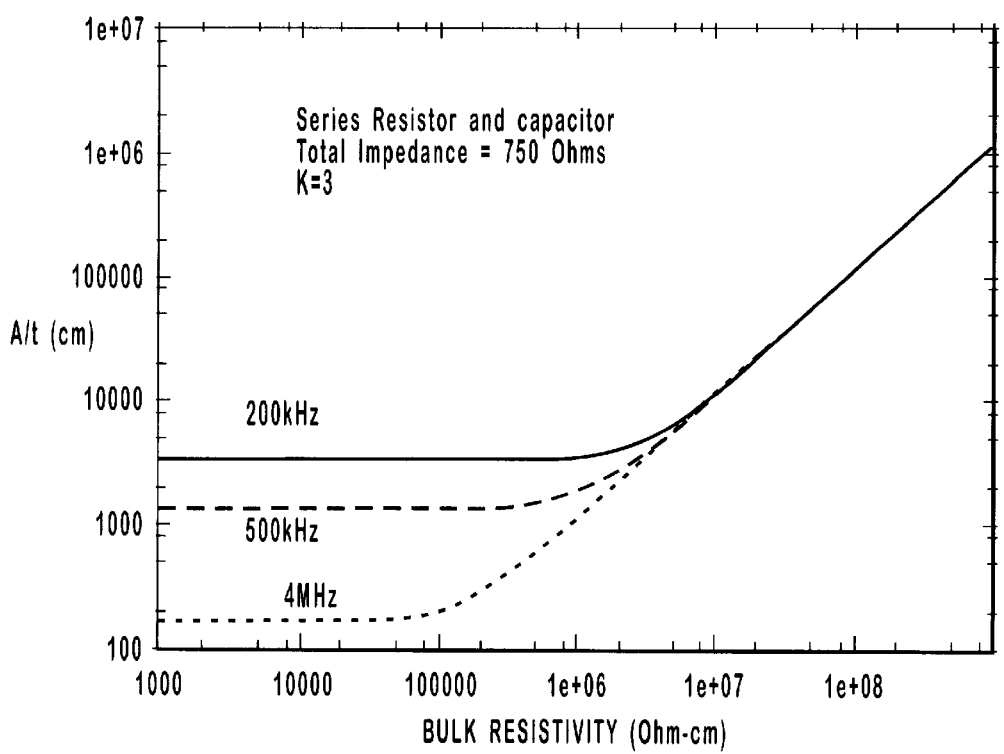
FIG. 14 is a graph showing bulk resistivity as a function of the area divided by the thickness of an electrosurgical return electrode in accordance with the present invention at various electrosurgical frequencies.

FIG. 14 plots A/t vs. bulk impedance $\eta$ for various electrosurgical frequencies. The y axis has the minimum ratio of A/t in order to have self-limiting behavior as a function of the bulk impedance. Note that we require bulk impedance always greater than 4000 Ω·cm. On the right hand side of the plot, all of the curves merge into one. In this regime, the total impedance of the circuit is dominated by the resistive component and is, hence, independent of frequency. On the left hand side, the circuit impedance is dominated by the capacitive conduction of current. One requires area to thickness ratios of several hundred to about 10,000 in order to provide sufficient total impedance with the low ohmic resistance in this region.

The resulting lowest possible bulk impedance, therefore, is greater than that anticipated by U.S. Pat. No. 4,088,133, issued to Twentier; and, consequently, the self-limiting electrode according to the invention hereof appears to be neither taught nor suggested by known prior art. A product according to the invention hereof can be easily distinguished from previous art through a simple test of the bulk impedance, such as the bulk resistivity of the insulating material, independent of electrode area or electrode thickness.

Interrelationships of Geometries Materials and Power Sources

As mentioned above, FIGS. 11–17 are set forth to define the geometries and characteristics of materials employed to obtain the foregoing self-limiting action. Discussion will be made hereinafter to present illustrative information and an example related to an electrode that may be used for electrosurgical procedures utilizing capacitive conduction while still remaining self-limiting. Although discussion is made herein with respect to an electrosurgical electrode functioning under capacitive conduction, similar illustrative information and examples may be provided for resistive and inductive conduction, as known by one skilled in the art.

Figure 15:
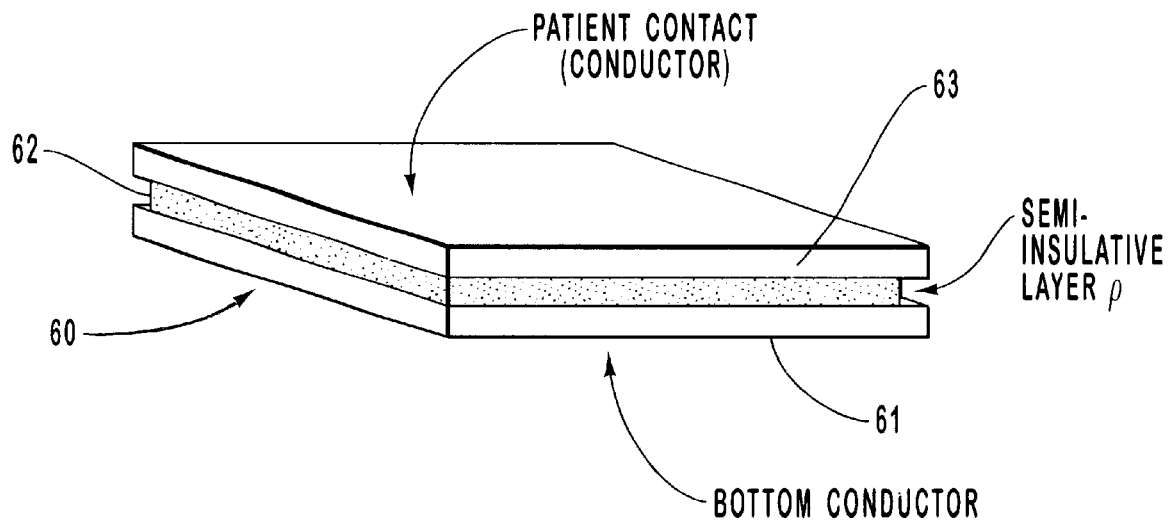
FIG. 15 is a perspective view illustrating, for the purpose of analysis, the circuit equivalent of a patient in operative association with the ohmic and capacitive regions of an electrode according to the invention.
Figure 16:
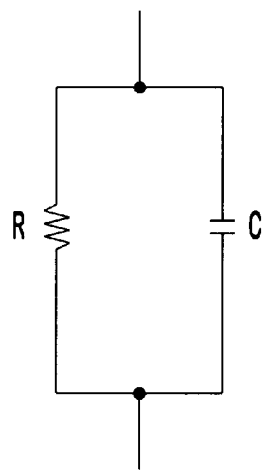
FIG. 16 is a simple electronic schematic circuit equivalent to FIG. 15.

FIG. 15 depicts an electrosurgical electrode 60 consisting of a conductive metal backing 61 and a semi-insulating layer 62 of material with bulk resistivity $\rho$, thickness t and area A. The electrode is in contact with another conducting layer 63 that represents a patient thereupon. The circuit can be modeled as a resistor R in parallel with a capacitor C (FIG. 16). The resistance R is related to the bulk resistivity $\rho$, area A, and thickness t by the formula $$R = \frac{\rho t}{A} \tag{26}$$

The capacitance C is approximately related to the area A, thickness t, permittivity constant $\varepsilon_0 = 8.85 \times 10^{-12}$ F/m and the dielectric constant of the material $\kappa$:

$$C = \frac{\kappa \varepsilon_0 A}{t} \tag{27}$$

The magnitude of the capacitor impedance is:

$$X_C = \frac{1}{\omega C} = \frac{t}{\omega \kappa \varepsilon_0 A} \tag{28}$$

The ratio Y of the current flow due to the capacitive path to the current flow due to the resistive path is $$Y = \frac{\frac{1}{X_C}}{\frac{1}{R}} = \frac{\frac{\omega \kappa \varepsilon_0 A}{t}}{\frac{A}{\rho t}} = \omega \kappa \varepsilon_0 \rho \tag{29}$$

The ratio Y is independent of the electrode area and thickness, depending only upon $\kappa$ and $\rho$. For principally capacitive coupling, Y>>1, whereas for principally resistive current, Y<<1 the boundary between the capacitive current and the resistive current is Y=1.

$$1 = 2\pi f \kappa \varepsilon_0 \rho \tag{30}$$

We can use this, along with the value of $\varepsilon_0$, to find the necessary values of $\rho$ for capacitive conduction, given nominal values of $\kappa$ and $\omega = 2\pi f$ where f is the electrosurgical generator frequency.

$$\rho = \frac{1}{2\pi f \kappa \varepsilon_0} \quad (31)$$

For most insulating materials, κ ranges from 3 to 5. Commercially available electrosurgical generators presently have operating frequencies ranging from 200 kHz to 4 MHz. For κ=5 and f=4 MHz, it is preferred that $\rho \geq 1 \times 10^5$ Ω·cm for the electrosurgical electrode to return the majority of its current through capacitive coupling. For κ=3 and f=200 kHz, we require $\rho \geq 3 \times 10$ Ω·cm.

The percentage of total current derived through capacitive coupling is given by $$\text{pct} = \frac{\frac{1}{|X_C|^2}}{\frac{1}{|R|^2} + \frac{1}{|X_C|}} = \frac{|R|^2}{|R|^2 + |X_C|^2} = \frac{\left(\frac{\rho t}{A}\right)^2}{\frac{(\rho t)^2}{A} + \left(\frac{t}{A\varepsilon_0 \kappa \omega}\right)^2} \quad (32)$$

$$= \frac{\rho^2}{\rho^2 + \left(\frac{1}{\varepsilon_0 \kappa \omega}\right)^2} = \frac{(\varepsilon_0 \kappa \omega \rho)^2}{(\varepsilon_0 \kappa \omega \rho)^2 + 1}$$

Figure 17:
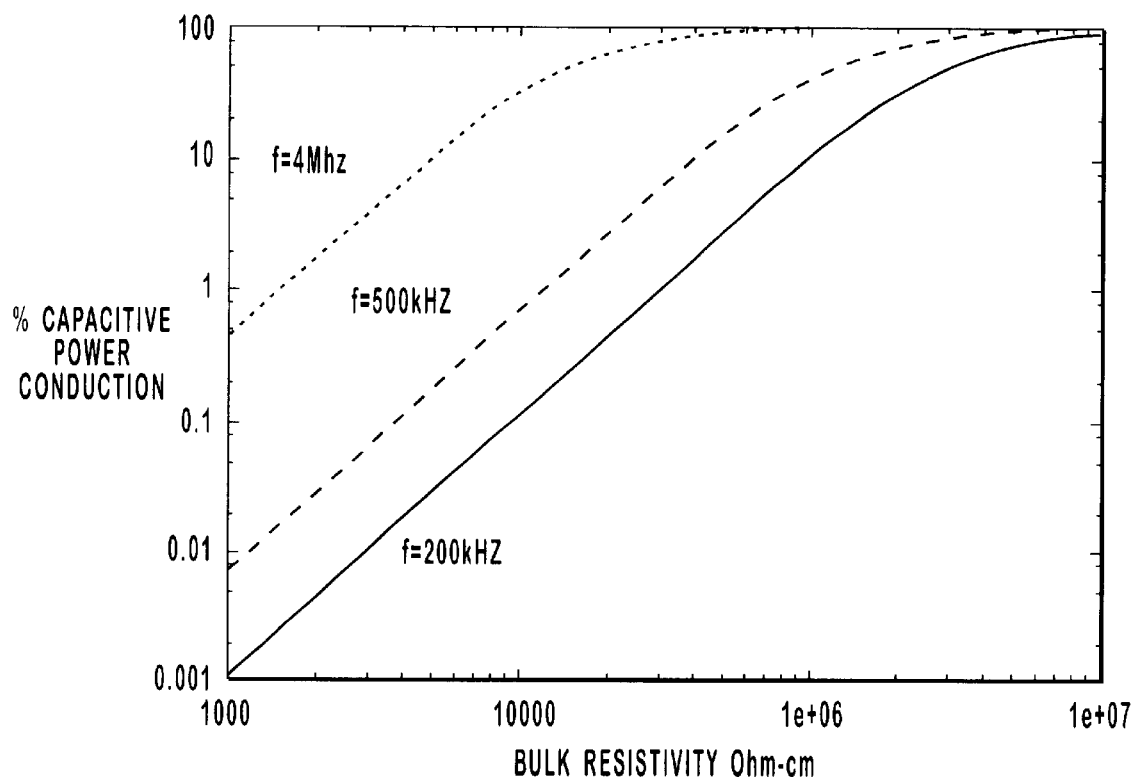
FIG. 17 is a graph depicting percent capacitive power conduction as a function of bulk resistivity of the resistive layer for different electrosurgical operating frequencies.

FIG. 17 illustrates the percentage (%) of capacitive coupling for various frequency electrosurgical generators. At the extreme (4 MHz), a minimum bulk impedance of $10^5$ Ω·cm is required for the majority of the current to be passed through capacitive coupling.

Electode with Pressure Reducing Capabilities

Referring now to FIGS. 18–23, various other alternate embodiments of the present invention are depicted. The electrosurgical electrodes illustrated in FIGS. 18–23 are self-limiting to prevent burning of a patient during an electrosurgical procedure and can include a pad that helps to reduce the possibility of decubitus ulcer or pressure sore creation that may arise during prolonged surgical procedures. By combining self-limiting characteristics and pressure sore reduction properties the electrosurgical electrodes of the present invention protect patients during all types of surgical procedure from the creation of pressure sores, while providing the benefits of a self-limiting electrosurgical electrode as described herein. Optionally, the electrosurgical electrodes of the present invention can include heating and/or cooling capabilities or characteristics that enable the electrosurgical electrode to heat and/or cool a patient during a surgical procedure. Such heating and/or cooling characteristics can be optionally combined with the electrosurgical electrode and/or the pad that limits the creation of decubitus ulcers or pressure sores during prolonged surgical procedures.

Figure 18:
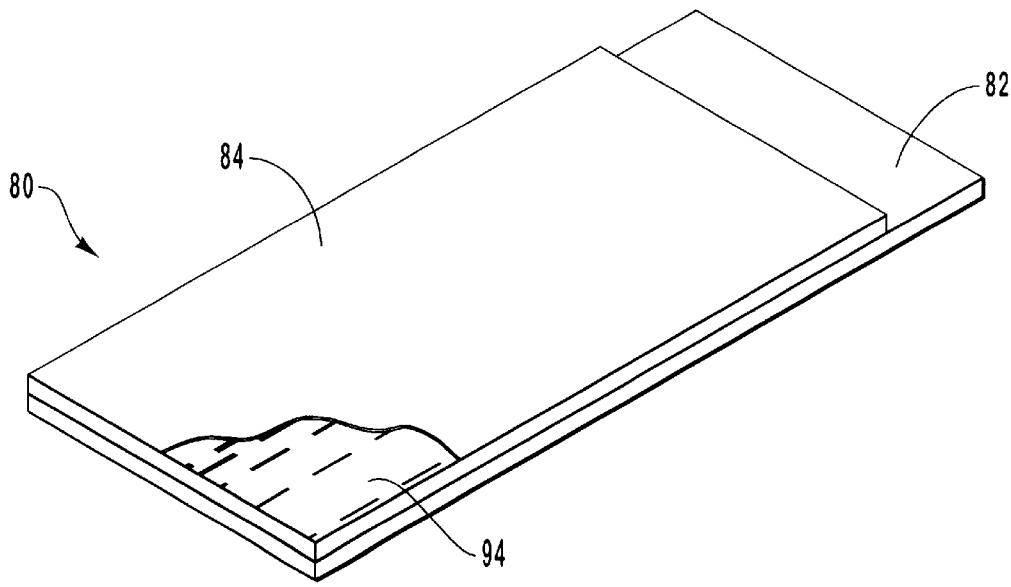
FIG. 18 is a perspective view of a bedsore/ulcer pad including a self limiting electrosurgical return electrode illustrating the principles of the present invention.
Figure 19:
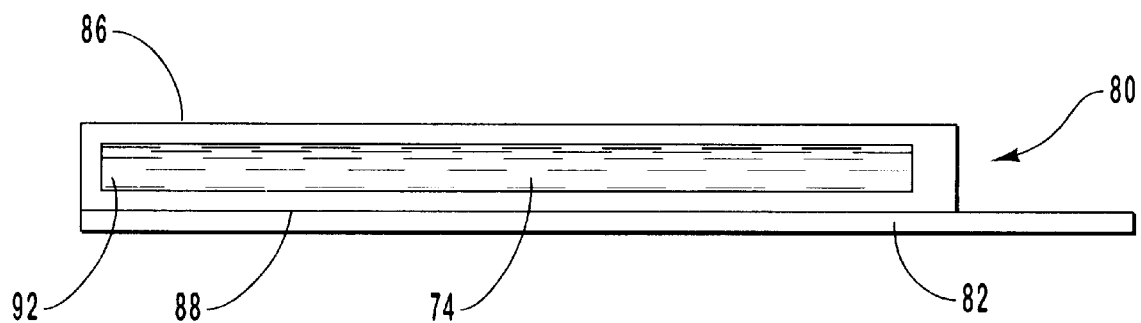
FIG. 19 is a side view of the section taken along the lines 19—19 of FIG. 18.

Referring specifically to FIGS. 18 and 19, an electrosurgical electrode 80 is depicted. Electrosurgical electrode 80, in one embodiment, includes a conductive element or electrode 82 and a pad 84. Electrode 82, in one configuration, is made of a conductive plastic, rubber or other flexible material which, when employed as a conductive element, will result in an effective DC resistance presented by each square centimeter of the working surface of electrosurgical electrode 80 (the surface that is in contact with or in close proximity to the patient) to be greater than about 8000 ohms or alternatively provide a bulk impedance of greater than 4000 Ω·cm. Various materials may be appropriate to give the required impedance. For example, silicone or butyl rubber have been found to be particularly attractive materials for electrode 82 as they are flexible, as well as readily washable, disinfectable, and sterilizable. Alternatively, in another embodiment, electrode 82 may be made of an inherently relatively high resistance flexible material altered to provide the requisite conductivity. One example of the latter is that of silicone rubber material in which there are impregnated conductive fibers, such as carbon black, quantities of gold, silver, nickel, copper, steel, iron, stainless steel, brass, aluminum, or other conductors.

In yet another alternate configuration, electrode 82 may be fabricated from a material that is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows electrode 82 and electrosurgical electrode 80, when the other components of electrosurgical electrode 80 are transparent to one or more wavelengths of electromagnetic radiation, to be maintained in place during performance of certain medical procedures using particular wavelengths of electromagnetic radiation.

It may be appreciated by one skilled in the art that electrode 82 may have various other configurations so long as electrode 82 is capable of performing the functions of an electrode, i.e., being capable of passing current therethrough. For example, in another embodiment, electrode 82 includes a thin highly conductive lower stratum that facilitates connection of electrosurgical electrode 80 to an electrosurgical radio frequency energy source (not shown). In another alternate embodiment, electrode 82 is configured from multiple layers of conductors. In still yet another embodiment, electrode 82 includes an outer dielectric layer that substantially surrounds an interior-conducting layer, similar to the electrosurgical electrodes described previously.

Referring again to FIG. 18, attached to electrode 82 is pad 84. As shown in FIG. 19, pad 84 has an upper surface 86 and a lower surface 88 that define an interior chamber 92 therebetween. Upper surface 86 is configured to be placed against the surface of a patient (thereby acting as the working surface of electrosurgical electrode 80), while lower surface 88 is connected to electrode 82. In this manner, pad 84 supports and distributes the weight and downward forces of a patient positioned upon pad 84 throughout the entire pad to reduce the possibility of pressure sore creation. Lower surface 88 may be alternatively adapted to rest upon either the patient or a structure upon which the patient is resting, such as an operating table, a chair, or the like. Similarly, upper surface 86 may be configured to connect to electrode 82.

Filling interior chamber 92 of pad 84 is material 94. Material 94 provides pad 84 with pressure reducing characteristics. More specifically, since a defined volume of material 94 is retained within interior chamber 92, when an individual rests upon pad 84, material 94 distributes the downward force of the patient throughout material 94, thereby decreasing the point forces applied to those parts of the patients anatomy where bony prominences are located. In this manner, pad 84 reduces the pressure exerted upon the patient and thereby limits the generation of pressure sores. Optionally, instead of only material 94 providing the pressure reducing characteristics, a combination of material 94, the material forming pad 84, and/or the materials forming electrode 82 can provide the pressure reducing characteristics of the present invention.

According to another aspect of the present invention, material 94 may act as a dielectric layer to reduce the current that flows through pad 84. Alternatively, material 94 may take the form of a conducting material to aid with the transmission of current therethrough. Additionally, material 94 may provide a thermal mass for the distribution of heat during an electrosurgical procedure. As discussed above, AAMI requires that during an electrosurgical procedure the temperature rise of the patient's tissue should remain below six degrees Celsius (6° C.). The thermal mass provided by material 94 assists with the distribution of heat throughout the patient's body and substantially eliminates, in combination with the self-limiting characteristics of electrosurgical electrode 80, the potential for hot spots that may burn the patient. Consequently, the substances used for material 94 may perform multiple functions during an electrosurgical procedure.

In general, material 94 may take the form of one or more solids, liquids, gases, or combinations thereof depending on the pressure reducing, dielectric, and/or conducting properties needed for electrosurgical electrode 80. For example, in one illustrative embodiment, material 94 is an elastomeric gel having a low durometer level, such as sorbethane. In addition to sorbethane, various other elastomeric gels may used, such as but not limited to those based upon the polymer chemistry of urethanes, silicones, hydrophilic elastomers or hydrogels, vinyls, vinyl alcohols, or other similar materials and technologies. Additionally, material 94 may take the form of water, saline, water based materials, conductive oils, and the like.

One skilled in the art may appreciate that there are various other configurations of pad 84 that may perform the desired function. For example, in another alternate embodiment, pad 84 is devoid of material 94 and is otherwise formed from a solid but flexible foam-type material. Consequently, pad 84 as a whole can provide the pressure reducing characteristics.

The pad 84 may be fabricated from various materials that are capable of being cleaned, sterilized, disinfected, and the like. Therefore, pad 84 may be manufactured from various types of materials, such as but not limited to, vinyl plastics, polyester, polyethylene, polyurethane, flexible sheet polymers, and the like. Generally, pad 84 has an approximate thickness of between about 0.5 to about 4 inches. It is preferable that pad 84 have a thickness of between about 0.5 to about 3 inches. It is more preferable that pad 84 has a thickness of between about 1 to about 2 inches.

The materials forming electrosurgical electrode 80, electrode 82, pad 84 and material 94, control the passage of current from electrode 82 to the patient. As such, in one embodiment, pad 84 and material 94 are insulative, while in an alternate configuration pad 84 and/or material 94 may be conductive and aid in the passage of current through the patient. So long as the total impedance of electrosurgical electrode 80 is within the limits defined herein, i.e., each square centimeter of the working surface being greater than 8000 ohms or bulk impedance greater than 4000 Ω·cm, the various elements of electrosurgical electrode 80, i.e., electrode 82, pad 84, and material 94, may provide one or more resistive, inductive, and/or capacitive inductance components to the bulk impedance. In this manner electrosurgical electrode 80 is self-limiting, while providing pressure reducing characteristics.

It may be appreciated by one skilled in the art that various other configurations of electrosurgical electrode 80 are applicable. For example, in another configuration, electrosurgical electrode 80 may be built into an operating room table or alternatively the operating room table cushion such that the operating table has pressure sore reduction capabilities and self-limiting capabilities during an electrosurgical procedures. In another configuration, electrosurgical electrode 80 need not be used for electrosurgical procedures but may be used as only an insulating pad or pressure sore pad. By so doing, creation of electrosurgical electrode 80 and the other related electrodes described herein reduce the need for a medical facility to purchase and store multiple different pressure sore pads and electrosurgical return electrodes. Additionally, the electrosurgical electrode may be used multiple times since it is sterilizable, cleanable, washable, and disinfectable. In another configuration of the present invention, electrosurgical electrode 80 may be used with other pressure sore devices, even though such other pressure sore devices have a number of disadvantages as described previously.

Generally, the configuration of electrosurgical electrode 80 allows a clinician to either place a patient on or beneath electrosurgical electrode 80. The weight of electrosurgical electrode 80 maintains electrosurgical electrode 80 in place during a surgical procedure. Even though other pressure sore devices have a various disadvantages, a clinician is able to combine electrosurgical electrode 80 with other pressure sore devices when electrosurgical electrode 80 is placed upon the patient. By creating a combined pressure sore pad and electrosurgical electrode, the bulk impedance may be defined thereby eliminating the possibility of reduced efficacy of an electrosurgical electrode when such an electrosurgical electrode is combined with other pressure sore devices with unknown bulk impedances.

Figure 20:
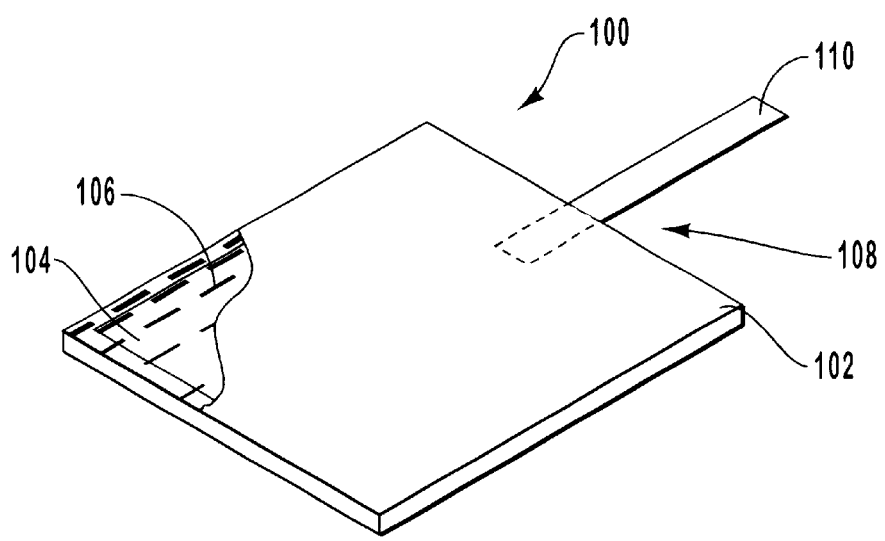
FIG. 20 is a section similar to that of FIG. 19 but illustrating the capacitance presented by a patient's surgical gown.

Referring now to FIG. 20, an alternate configuration of an electrosurgical electrode 100 is depicted. The majority of the features previously discussed with respect to the other electrosurgical return electrodes described herein also apply to electrosurgical electrode 100. Electrosurgical electrode 100 includes a pad 102 having an interior chamber 104 filled with a material 106 therein and a conductive element or electrode 108. Pad 102 is generally configured to cooperate with a patient, whether the patient is to be seated thereon, in a supine position, or some other position. In this embodiment, pad 102 is formed from a thin dielectric-providing material, such as, but not limited to, polyurethane, polyethylene, vinyl, or similar material that will contain material 106 within interior chamber 104.

Material 106 that fills interior chamber 104 provides an upward force against the downward force applied by a patient as he or she rests upon electrosurgical electrode 100 during a surgical procedure. In this manner, electrosurgical electrode 100 has pressure reducing characteristics that limit the possibility of a patient developing decubitus ulcers or pressure sores. Optionally, the combination of material 106, the material forming pad 102, and/or the materials forming electrode 108 can provide the pressure reducing characteristics of the present invention.

In this configuration, material 106 can act as a conductor to transfer current between the patient, the active electrode, and the electrosurgical unit (not shown) during various electrosurgical procedures. Optionally, material 106 may have a similar configuration and perform similar functions to material 94 and the other materials described herein Communicating with pad 102 and material 106 is electrode 108. Electrode 108 includes a contact 110 that allows electrode 108, and therefore electrosurgical electrode 100 to electrically couple with an electrosurgical radio frequency energy source or electrosurguical unit (not shown). Electrode 108, in this embodiment, is disposed within interior chamber 104 of a pad 102. Electrode 108 may be positioned against the bottom surface of interior chamber 104 of pad 102, centered or free floating inside interior chamber 104, against the top surface of interior chamber 104 of pad 102, formed on the interior surface of interior chamber 104, or any combination thereof. Electrode 108, in this embodiment, traverses a substantial portion of interior chamber 104. As depicted by the dotted lines, however, electrode 108 may partially enter interior chamber 104 to electrically communicate with material 106 filling interior chamber 104. Electrode 108 may, therefore, extend a substantial distance into interior chamber 104, partially extend into interior chamber 104, communicate with the interior surface of interior chamber 104, or any combination thereof.

Electrode 108, in this illustrative embodiment, can be a thin sheet of conductive material, such as but not limited to a copper coated polyester fabric material. Alternatively, electrode 108 may be one of a variety of other materials so long as electrode 108 is capable of conducting electrical current, while having the desired flexibility. Electrode 108, therefore, may be a conductive or impregnated plastic, rubber, or other flexible material, a metal, a composite material, a mixture of two or more metals, and the like. In yet another embodiment, electrode 108 includes a conductive material that is sandwiched between two polymer sheets, similar to the electrosurgical return electrodes described previously.

Figure 21:
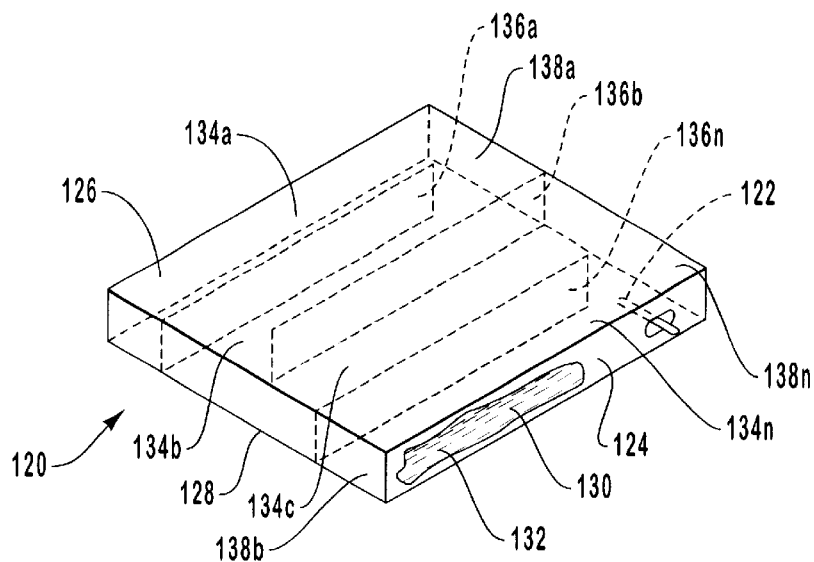
FIG. 21 is a perspective view of an alternate embodiment of a bedsore/ulcer pad including a self-limiting electrosurgical return electrode illustrating the principles of the present invention.

Referring now to FIG. 21, another alternate configuration of an electrosurgical electrode 120 is depicted. The majority of the features previously discussed with respect to the other electrosurgical return electrodes described herein also apply to electrosurgical electrode 120. As depicted, therefore, electrosurgical electrode 120 includes a conductive element or electrode 122 and a baffled pad 124.

Baffled pad 124, in this embodiment, is configured to help reduce the possibility of decubitus ulcers or pressure sores being created during prolonged surgical procedures. As illustrated, baffled pad 124 has a generally rectangular body, although baffled pad 124 may have various other configurations and cross-sectional shapes as known to one skilled in the art in light of the teaching contained herein.

The baffled pad 124, in this configuration, has an upper surface 126 configured to contact a patient and a lower surface 128 distal from upper surface 126 that is configured to contact the surface upon which the patient is to rest, such as an operating table, cart, or the like. Disposed between upper surface 126 and lower surface 128 is an interior chamber 130 that is filled with a material 132. The interior chamber 130, in one embodiment, is divided into a number of separate but connected subchambers 134a–134n by one or more baffles 136a–136n that extend substantially along the length (or alternatively the width) of baffled pad 124. Each baffle 136a–136n is configured to extend substantially along the length (or width) of baffled pad 124 while leaving an opening 138a–138n to allow adjacent subchambers 134a–134n to communicate one with another. In this manner, material 132 may fill and move between subchambers 134a–134n as a patient rests upon baffled pad 124.

Baffled pad 124, in one configuration, can be manufactured from one or more sheets of material that may be sewn, thermal bonded, or otherwise joined together or manipulated to create a sleeve-type construction. Further, baffled pad 124 and baffles 136a–136n may be fabricated from a variety of materials, such as but not limited to vinyl plastics, polyester, polyethylene, polyurethane, or similar materials. It may be appreciated that the body of baffled pad 124 can be fabricated from a different material than baffles 136a–136n so long as the body and baffles 136a–136n are capable of being joined or bonded together or otherwise cooperate to create baffled pad 124.

Further, the configuration of baffled pad 124 may have various other configurations as known by one skilled in the art. For example, in an alternate configuration, either upper surface 126 or lower surface 128 may be configured to contact a patient or the surface upon which the patient and electrosurgical electrode 120 is to rest. In another alternate configuration, each subchamber 134a–134n is an independent chamber and does not communicate with the other subchambers 134a–134n, thereby requiring separate filling with material 132. In yet another alternate configuration, one or more of subchamber 134a–134n lie along the longitudinal length of baffled pad 124, while one or more of subchamber 134a–134n lie substantially perpendicular to the longitudinal length of baffled pad 124 and communicate with those one or more subchambers 134a–134n that lie along the longitudinal length of baffled pad 124. In another configuration of the present invention, baffled pad 124 may include one or more openings through the body of baffled pad 124 that communicate with either interior chamber 130 or each individual subchamber 134a–134n thereof. As such, a user may access interior chamber 130 and input the necessary quantity of material 132 therein. Generally, the orientation and configuration of each subchamber 134a–134n may vary as required by a user of electrosurgical electrode 120.

As referenced above, each subchamber 134a–134n may be filled with material 132. Material 132 is configured to provide a force that opposes the downward force of a patient resting upon electrosurgical electrode 100. Consequently, material 132 alone or in combination with the material forming baffled pad 124, and/or the materials forming electrode 122 can provide the pressure reducing characteristics of the present invention. Further, material 132 may have various configurations ranging from solids, liquids, gases, and combinations thereof. The material 132, therefore, may have a similar configuration and function to the other materials described herein.

In the illustrated configuration of FIG. 21, during use of electrosurgical electrode 120, interior chamber 130 is filled with material 132 that provides cushioning to a patient to prevent pressure sore creation. It may be understood that baffled pad 124 need not contain material 132 within interior chamber 130 at all times but may be devoid of the requisite material 132 during shipping and storage of baffled pad 124, while being configured with one or more openings therein to all the addition of material 132 or a component thereof at some subsequent time. For example, in one configuration, material 132 is a solid material stored within one or more of subchambers 134a–134n that converts to a liquid, fluid, gas, or gelatinous material when a liquid is introduced to the solid material through one or more openings.

According to another aspect of the present invention, material 132 may be an insulative or conductive material depending on the configuration of electrode 122. Therefore, material 132 may be insulating or conducting, thereby optionally providing resistive, inductive, and/or capacitive impedances to electrosurgical electrode 120. Material 132 may be an elastomeric gel having a low durometer level, such as sorbethane, an elastomeric gel based polymer chemistry of urethanes, silicones, hydrophilic elastomers or hydrogels, vinyls, vinyl alcohols, or other similar materials and technologies, water, saline, water based materials, conductive oils, and the like.

As illustrated in FIG. 21, attached to baffled pad 124 is electrode 122. Electrode 122 may have one or more of the various configurations previously discussed herein and known by one skilled in the art. For example, electrode 122 can be formed on the surface of interior chamber 130 and include a conductor 138 that extends through the body of baffled pad 124 to communicate with an electrosurgical unit (not shown). Alternatively, electrode 122 can be wholly or partially retained within baffled pad 124, in a similar manner to that described herein. In still another alternate embodiment of the present invention, electrode 122 can have the form of electrode 82, such that electrode 122 is attached to either upper surface 126 or lower surface 128 of baffled pad 124.

Figure 22:
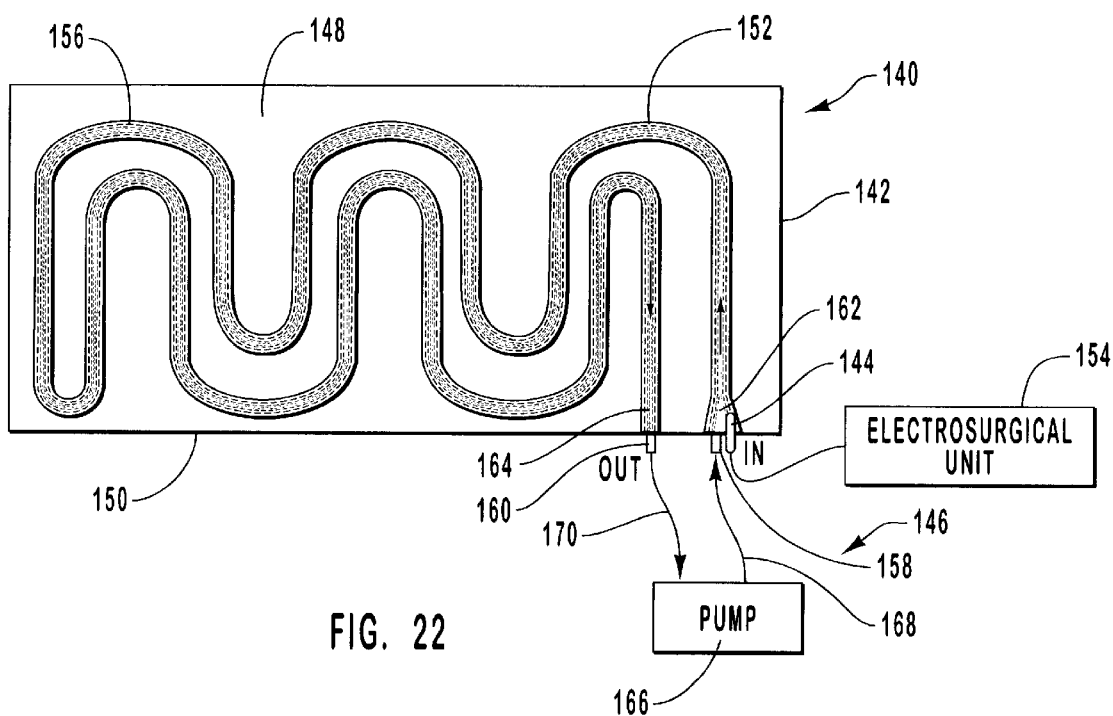
FIG. 22 is a side view of another alternate embodiment of a bedsore/ulcer pad including a self-limiting electrosurgical return electrode illustrating the principles of the present invention.

Referring now to FIG. 22, an alternate configuration of an electrosurgical electrode 140 is depicted. The majority of features previously discussed with respect to the other electrosurgical electrodes described herein also apply to electrosurgical electrode 140. Electrosurgical electrode 140, in one embodiment, includes a sleeve 142, an electrode 144, and a pump assembly 146.

Sleeve 142 is configured to perform similar functions to the pads described herein, i.e., sleeve 142, either alone or in combination with electrode 144 and/or the material contained within sleeve 142 helps to limit the creation of decubitus ulcers or pressure sores that may arise during prolonged surgical procedures. Further, sleeve 142 illustrates one configuration of an electrosurgical electrode that can provide heating and cooling characteristics or functionality and thereby provide an electrode that can heat and/or cool a patient during surgical procedures.

As illustrated, sleeve 142 includes an upper surface 148 and a lower surface 150 that are separated one from another and define an interior chamber 152 therebetween. Upper surface 148, in this embodiment, is configured to allow a patient to rest thereupon, while lower surface 150 is configured to rest upon a support platform, such as an operating table, upon which electrosurgical electrode 140 is placed during an electrosurgical operation. It may be appreciated that the functions and configurations of upper and lower surfaces 148, 150 may be reversed, while electrosurgical electrode 140 need not be used solely during electrosurgical operations but may be used at any time cushioning of a patient is needed.

As illustrated in FIG. 22, interior chamber 152 may be filled with a material 156. Material 156 may have a similar configuration as one or more of the other materials described herein and known to one skilled in the art in light of the teaching contained herein.

Extending from sleeve 142 is an inlet connector 158 and an outlet connector 160 that are adapted to communicate with pump assembly 146. Inlet connector 158 communicates with a first end 162 of interior chamber 152, while outlet connector 160 communicates with a second end 164 of serpentine interior chamber 152, such that material 156 may be input through inlet connector 158 and exit sleeve 16=42 and interior chamber 152 through outlet connector 160.

It may be appreciated by one skilled in the art that the number and configuration of inlet and outlet connectors 158, 160 may vary dependent on the particular configuration of sleeve 142. For example, in an alternate configuration sleeve 142 may include a plurality of serpentine chambers 152 and include one or more inlet connectors 158 and one or more outlet connectors 160. In still another configuration, interior chamber 152 may only partially fill the interior chamber 152 of sleeve 142.

Electrically communicating with interior chamber 152 is electrode 144. Electrode 144 may have one or more of the various configurations previously discussed herein and known by one skilled in the art. For example, as illustrated in FIG. 22, electrode 144 may extend into interior chamber 152, while extending through the body of sleeve 142 to communicate with an electrosurgical unit 154. In another configuration, electrode 144 may be attached to either upper surface 148 or lower surface 150 of sleeve 142.

Pump assembly 146, in one configuration, includes a pump 166 that communicates with sleeve 142 via an inlet pipe 168 and an outlet pipe 170. Pump 166 can be a water pump, an air pump, a liquid pump, a fluid pump, or the like that is used to circulate material 156 received from a storage container (not shown) through sleeve 142. The material 156 stored within the storage container (not shown) and circulated through sleeve 142 can have a similar configuration and perform similar functions to the other materials described herein.

According to another aspect of the present invention, pump 166 may optionally heat and/or cool material 156 as material 156 passes through pump 166. Consequently, electrosurgical electrode 140 can optionally heat and/or cool a patient resting upon sleeve 142 during a surgical procedure. It can be appreciated by one skilled in the art that pump assembly 146 and the other elements of electrosurgical electrode 140 may have various other configurations as known by one skilled in the art in light of the teaching contained herein.

As implied above, any of the electrosurgical electrodes described herein can incorporate the functionality of heating and/or cooling as described herein. Therefore, such electrosurgical electrode may heat and/or cool a patient during surgical procedures, whether or not the electrosurgical electrode limits the creation of decubitus ulcers or pressure sores.

Figure 23:
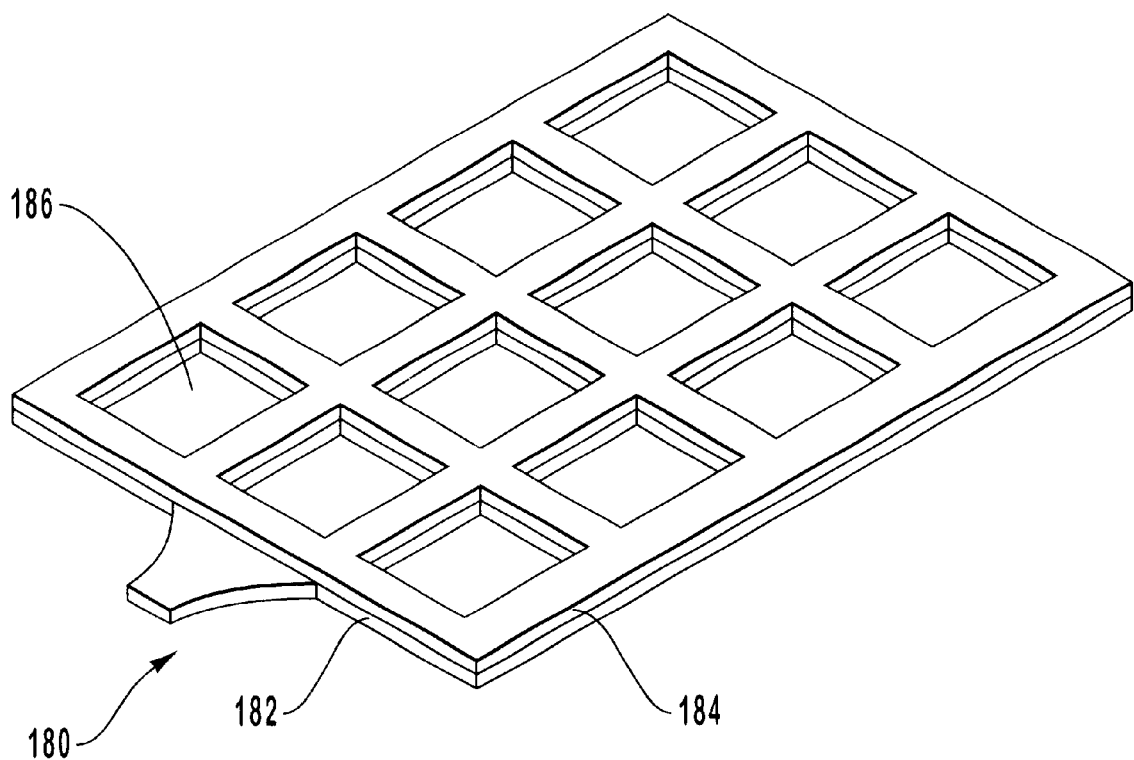
FIG. 23 is a perspective view of yet another alternate embodiment of a bedsore/ulcer pad including a self-limiting electrosurgical return electrode illustrating the principles of the present invention.

Referring now to FIG. 23, an alternate configuration of an electrosurgical electrode 180 is depicted. The majority of the features previously discussed with respect to the electrosurgical electrodes described herein also apply to electrosurgical electrode 180.

Electrosurgical electrode 180, in one configuration, includes an electrode 182 and a pad 184. Electrode 182, in one configuration, is made of a conductive plastic, rubber or other flexible material that will result in an effective DC resistance presented by each square centimeter of the working surface of the electrode to be greater than about 8000 ohms. The pad 184 of electrosurgical electrode 180 may have any configuration consistent with the other pads and disclosure contained herein. For instance, pad 184 may include an interior chamber that is filled with a material that helps to reduce the possibility of decubitus ulcer or pressure sore creation that may arise during prolonged surgical procedures. In addition, pad 184 may provide heating and cooling capabilities that allow a patient resting upon pad 184 20 to be heated or cooled during a surgical procedure.

Additionally, electrode 182 and pad 184, in this configuration, may have one or more holes 186 therein, such that electrosurgical electrode 180 has a lattice-type structure. The inclusion of one or more holes 186 increases the flexibility of electrosurgical electrode 180. By providing increased flexibility, electrosurgical electrode 180 is more easily adaptable to the contours of a patient's body and any surface upon which the patient is resting. It may be appreciated that the functionality and structures associated with electrosurgical electrode 180 may be incorporated within any of the other electrosurgical electrodes described herein. Further, there are various manners by which electrode 182 may be configured to be flexible. For example, electrode 182 may be formed from a mesh material that provides the necessary flexibility. In yet another configuration, electrode 182 may be a flexible solid piece of conductive material.

It will now be evident that there has been described herein an improved electrosurgical electrode characterized by being generally electrode-shaped and including a conformable pad. The improved electrosurgical electrode evidencing the features of being self-limiting while being reusable, readily cleanable and obviating the necessity for use of conducting gels or supplementary circuit monitoring equipment, while providing a conformable platform upon which a patient may rest that reduces the incidence of pressure sores. Further, the improved electrosurgical electrode provides the features of heating and/or cooling to thereby heat and/or cool a patient during a surgical procedure or during recovery of the patient. Similarly, the electrosurgical electrodes of the present invention can be utilized during any surgical procedure, during recovery of the patient from the surgical procedure, while the patient is hospitalized, or the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An electrosurgical electrode comprising:
   (a) a pad configured to substantially prevent the creation of one or more pressure sores on a patient resting upon said pad; and
   (b) a conductive element configured to electrically communicate with said pad and configured to conduct electrical current
   wherein, said pad and said conductive element collectively have an effective bulk impedance equal to or greater than about 4,000 $\Omega \cdot cm$.

2. An electrosurgical electrode according to claim 1, wherein said conductive element comprises electrically conducting material having an effective bulk impedance equal to or greater than about 4,000 $\Omega \cdot cm$.

3. An electrosurgical electrode according to claim 1, wherein said pad comprises electrically conducting material having an effective bulk impedance equal to or greater than about 4,000 $\Omega \cdot cm$.

4. An electrosurgical electrode according to claim 1, wherein said pad comprises a dielectric material.

5. An electrosurgical electrode according to claim 1, wherein said pad comprises a conducting material.

6. An electrosurgical electrode according to claim 1, wherein said pad comprises an elastomeric material.

7. An electrosurgical electrode according to claim 1, wherein said pad comprises a dielectric material and a conducting material.

8. An electrosurgical electrode according to claim 1, wherein said pad comprises an interior chamber and one or more baffles disposed with said interior chamber.

9. An electrosurgical electrode according to claim 1, wherein said pad and said conducting element comprises a lattice structure.

10. An electrosurgical electrode according to claim 1, wherein said pad comprises a port in communication with an interior chamber, said port being configured to allow a material to circulate through said interior chamber.

11. An electrosurgical electrode according to claim 1, wherein said conductive element comprises normally insulating material impregnated with electrically conducting fibers to render the electrosurgical electrode to have an effective bulk impedance equal to or greater than about 4,000 $\Omega \cdot cm$.

12. An electrosurgical electrode according to claim 1, wherein said pad comprises normally insulating material impregnated with electrically conducting fibers to render said sheet to have an effective bulk impedance equal to or greater than about 4,000 $\Omega \cdot cm$.

13. An electrosurgical electrode according to claim 1, wherein said collective effective bulk impedance of said pad and said conductive element comprises electrical components selected from the group consisting of resistance, capacitive, inductive, and combinations thereof.

14. An electrosurgical electrode according to claim 1, wherein said conductive element comprises:
   (a) an electrode, said electrode comprising:
      (i) a first layer of predetermined limited electrical conductivity; and
      (ii) a second layer of dielectric material having a predetermined capacitive reactance, said second layer contacting and overlying said first layer.

15. The electrosurgical electrode according to claim 1, wherein said pad comprises a working surface for being positioned in contact with or in close proximity to a patient.

16. The electrosurgical electrode according to claim 1, wherein said conductive element comprises a working surface for being positioned in contact with or in close proximity to a patient.

17. The electrosurgical electrode according to claim 15 or 16, wherein said working surface having a surface area within a range from about 11 to about 1500 square inches.

18. An electrosurgical electrode according to claim 1 wherein the electrode is sterilizable.

19. An electrosurgical electrode according to claim 1 wherein the electrode is washable.

20. An electrosurgical electrode according to claim 1 wherein the electrode is reusable.

21. An electrosurgical electrode according to claim 1 wherein the electrode is disinfectable.

22. The electrosurgical electrode according to claim 1, further comprising a sleeve substantially enclosing said pad and said conductive element.

23. An electrosurgical electrode for preventing the creation of pressure sores on a patient resting upon the electrosurgical electrode, the electrosurgical electrode comprising:
   (a) a pad having an interior chamber therein, said interior chamber being filled with a material; and
   (b) a conductive element coupled to said pad and configured to conduct electrical current through said pad;
   wherein, the collective bulk resistance of said pad and said conductive element is equal to or greater than about 4,000 $\Omega \cdot cm$.

24. An electrosurgical electrode according to claim 23, wherein said conductive element comprises electrically conducting material having an effective bulk resistivity equal to or greater than about 4,000 $\Omega \cdot cm$.

25. An electrosurgical electrode according to claim 23, wherein said conductive element comprises normally insulating material impregnated with electrically conducting fibers to render said sheet to have an effective bulk resistivity equal to or greater than about 4,000 $\Omega \cdot cm$.

26. An electrosurgical electrode according to claim 23, wherein said conductive element comprises:
(a) an electrode, said electrode comprising:
(i) a first layer of predetermined limited electrical conductivity; and
(ii) a second layer of dielectric material having predetermined impedance,
said second layer contacting and overlying said first layer.

27. An electrosurgical electrode according to claim 23, wherein said pad comprises a working surface for being positioned in contact with or in close proximity to a patient.

28. An electrosurgical electrode according to claim 23, wherein said conductive element comprises a working surface for being positioned in contact with or in close proximity to a patient.

29. An electrosurgical electrode according to claim 27 or 28, wherein said working surface having a surface area within a range from about 11 to about 1500 square inches.

30. An electrosurgical electrode according to claim 23, wherein the electrode is sterilizable, washable, reusable, disinfectable, or disposable.

31. An electrosurgical electrode according to claim 23, further comprising an insulating sleeve substantially enclosing said pad and said conductive element.

32. An electrosurgical electrode according to claim 23 further comprising connecting means for making electrical connection with said conductive element.

33. An electrosurgical electrode according to claim 23, wherein said material comprises a dielectric material.

34. An electrosurgical electrode according to claim 23, wherein said material comprises a conducting material.

35. An electrosurgical electrode according to claim 23, wherein said material comprises an elastomeric material.

36. An electrosurgical electrode according to claim 23, wherein said interior chamber comprises one or more sub-chambers defined by one or more baffles.

37. An electrosurgical electrode according to claim 36, wherein said one or more sub-chambers communicate one with another.

38. An electrosurgical electrode according to claim 23, wherein said pad and said conductive element comprises a lattice structure, said lattice structure configured to provide the electrosurgical electrode with flexibility.

39. An electrosurgical electrode according to claim 23, wherein said pad comprises an inlet port and an outlet port in communication with said interior chamber, said inlet port and said outlet port being configured to assist with the circulation of said material through said interior chamber.

40. An electrosurgical electrode according to claim 39, further comprising a pump assembly communicating with said inlet port and said outlet port, said pump assembly being configured to circulate said material through said interior chamber.

41. An electrosurgical electrode according to claim 40, wherein said pump assembly is configured to reduce the temperature of said material as said material passes through said pump assembly.

42. An electrosurgical electrode according to claim 40, wherein said pump assembly is configured to increase the temperature of said material as said material passes through said pump assembly.

43. An electrosurgical electrode for use during surgical procedures, the electrosurgical electrode comprising:
(a) a pad having an interior chamber therein, said interior chamber being filled with a material; and
(b) a conductive element coupled to said pad and configured to conduct electrical current through said pad;
wherein, the collective bulk resistance of said pad and said conductive element is equal to or greater than about 4,000 $\Omega \cdot cm$.

44. An electrosurgical electrode according to claim 43, wherein said pad comprises an inlet port and an outlet port in communication with said interior chamber, said inlet port and said outlet port being configured to assist with the circulation of said material through said interior chamber.

45. An electrosurgical electrode according to claim 44, further comprising a pump assembly communicating with said inlet port and said outlet port, said pump assembly being configured to circulate said material through said interior chamber.

* * * * *

UNITED STATES PATENT AND TRADEMARK OFFICE
CERTIFICATE OF CORRECTION

PATENT NO.    : 6,544,258 B2
DATED         : April 8, 2003
INVENTOR(S)   : Richard P. Fleenor et al.

It is certified that error appears in the above-identified patent and that said Letters Patent is hereby corrected as shown below:

Column 3,
Line 48, before "is thereby" change "patent" to -- patient --

Column 4,
Line 23, after "patient" change "bums" to -- burns --
Line 35, after "washable," change "disenfectable" to -- disinfectable --

Column 12,
Line 61, before "upper" change "their" to -- his of her --

Column 16,
Line 63, before "reduced" delete "22".

Column 21,
Line 30, before "with Pressure" change "Electode" to -- Electrode --

Column 23,
Line 21, after "gels may" insert -- be --

Column 24,
Line 20, before "various" delete "a"
Line 64, before "unit" change "electrosurguical" to -- electrosurgical --

Column 28,
Line 55, before "to be heated" delete "20"

Signed and Sealed this

Sixteenth Day of December, 2003

JAMES E. ROGAN
*Director of the United States Patent and Trademark Office*